(12) United States Patent
Hammer et al.

(10) Patent No.: US 7,504,561 B2
(45) Date of Patent: Mar. 17, 2009

(54) GDC-1 GENES CONFERRING HERBICIDE RESISTANCE

(75) Inventors: Philip E. Hammer, Cary, NC (US);
Todd K. Hinson, Rougemont, NC (US);
Brian Carr, Raleigh, NC (US);
Nicholas B. Duck, Apex, NC (US)

(73) Assignee: Athenix Corporation, Research Triangle Park, NC (US)

( * ) Notice: Subject to any disclaimer, the term of this patent is extended or adjusted under 35 U.S.C. 154(b) by 149 days.

(21) Appl. No.: 11/185,342

(22) Filed: Jul. 20, 2005

(65) Prior Publication Data
US 2006/0021093 A1    Jan. 26, 2006

Related U.S. Application Data

(63) Continuation-in-part of application No. 10/796,953, filed on Mar. 10, 2004, now abandoned.

(60) Provisional application No. 60/453,237, filed on Mar. 10, 2003.

(51) Int. Cl.
*C12N 15/82* (2006.01)
*C12N 15/52* (2006.01)

(52) U.S. Cl. .................... 800/300; 435/419; 435/320.1; 435/252.3; 536/23.2; 800/288; 800/298

(58) Field of Classification Search .................. None
See application file for complete search history.

(56) References Cited

U.S. PATENT DOCUMENTS 4,535,060 A    8/1985   Comai
4,769,061 A    9/1988   Comai
5,094,945 A    3/1992   Comai
5,188,642 A    2/1993   Shah et al.
5,463,175 A    10/1995  Barry et al.
6,448,476 B1   9/2002   Barry

FOREIGN PATENT DOCUMENTS

WO    WO 02/36782 A2    5/2002

OTHER PUBLICATIONS

Pojl et al 2002, Chem. Eur. J. 8(23): 5289-5295.*
Cataltepe et al 2007, Protein function prediction using motifs, sequence features, alighment scores. Eleventh Annual International Conference on Research in Computational Molecular Biology San Francisco Bay Area; Apr. 21-25, 2007.*

(Continued)

*Primary Examiner*—David H Kruse
(74) *Attorney, Agent, or Firm*—Alston & Bird LLP

(57) ABSTRACT

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed plants, plant cells, tissues, and seeds. In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising nucleotide sequences encoding an amino acid sequence shown in SEQ ID NO:3, 6, 8, 11, 19, or 21, or a nucleotide sequence set forth in SEQ ID NO:1, 2, 4, 5, 7, 9, 10, 18, or 20, as well as variants and fragments thereof.

14 Claims, 3 Drawing Sheets

OTHER PUBLICATIONS

Kishore, G.M., and Jacob, G.S., "Degradation of Glyphosate by *Pseudomonas* sp. PG2982 via a Sarcosine Intermediate," *J. Biol. Chem.*, Sep. 5, 1987, pp. 12164-12168, vol. 262, No. 25.

Shinabarger, D.L. and Braymer, H.D., "Glyphosate Catabolism by *Pseudomonas* sp. Strain PG2982," *J. Bacteriol.*, Nov. 1986, pp. 702-707, vol. 168, No. 2.

Wackett, L.P., et al., "Bacterial Carbon-Phosphorus Lyase: Products, Rates, and Regulation of Phosphonic and Phosphinic Acid Metabolism," *J. Bacteriol.*, Feb. 1987, pp. 710-717, vol. 169, No. 2.

NCBI Database Report for Accession No. AF098293, Direct Submission on Oct. 13, 1998.

EMBL Database Report for Accession No. CB901774, Apr. 26, 2003 (XP-002297562).

EMBL Database Report for Accession No. CF943872, Nov. 20, 2003 (XP-002297561).

Stalker, D.M., "Developing Herbicide Resistance in Crops by Gene Transfer Technology," *Plant Biotechnology*, vol. 1, 1990, pp. 82-104, Routledge, Chapman and Hall: New York, New York, USA and Blackie and Sons Ltd.: Glasgow, Scotland, UK.

Stock, M. et al., "Degradation of Glyphosate in Excised Leaves of Tobacco and Sugar Beet," *Journal of Plant Physiology*, 1991, pp. 171-174, vol. 139, No. 2.

\* cited by examiner

```
                          *        20         *        40         *        60         *
GDC-1(full : MASINIRVQNLEQPMDVAEYLFRRLHEIGIRSIHGLPGDYNPLALDYLPSCGLRWVGSVNELNAAYAADG :  70
GDC-1_(23) : ---------------------------------------------------------------------- :   -
GDC-1_(35) : ---------------------------------------------------------------------- :   -
GDC-1_(59) : ---------------------------------------------------------------------- :   -

80         *       100         *       120         *       140
GDC-1(full : YARVKQMGALITTFGVGELSAINGVAGAFSEHVPVVHIVGCPSTASQRNGMLLHHTLGNGDFNIFANMSA : 140
GDC-1_(23) : ---------------------------------------------------------------------- :   -
GDC-1_(35) : ---------------------------------------------------------------------- :   -
GDC-1_(59) : ---------------------------------------RNGMLLHHTLGNGDFNIFANMSA :  23

*       160         *       180         *       200         *
GDC-1(full : QISCEVAKLTNPAEIATQIDHALRVCFIRSRPVYIMLPTDMVQAKVEGARLKEPIDLSEPPNDPEKEAYV : 210
GDC-1_(23) : ---------------------------------------------------------------------- :   -
GDC-1_(35) : ---------------------------------------------------------------------- :   -
GDC-1_(59) : QISCEVAKLTNPAEIATQIDHALRVCFIRSRPVYIMLPTDMVQAKVEGARLKEPIDLSEPPNDPEKEAYV :  93

220         *       240         *       260         *       280
GDC-1(full : VDVVLKYLRAAKNPVILVDACAIRHRVLDEVHDLIEKTNLPVFVTPMGKGAVNEEHPTYGGVYAGDGSHP : 280
GDC-1_(23) : ---------------------------------------------------------------------- :   -
GDC-1_(35) : ---------------------------------------------------------------------- :   -
GDC-1_(59) : VDVVLKYLRAAKNPVILVDACAIRHRVLDEVHDLIEKTNLPVFVTPMGKGAVNEEHPTYGGVYAGDGSHP : 163

*       300         *       320         *       340         *
GDC-1(full : PQVKDMVESSDLILTIGALKSDFNTAGFSYRTSQLNTIDLHSDECIVKYSTYPGVQMRGVLRQVIKQLDA : 350
GDC-1_(23) : ---------------------------------------------------------------------- :   -
GDC-1_(35) : -------------------------------------------------TYPGVQMRGVLRQVIKQLDA :  20
GDC-1_(59) : PQVKDMVESSDLILTIGALKSDFNTAGFSYRTSQLNTIDLHSDECIVKYSTYPGVQMRGVLRQVIKQLDA : 233

360         *       380         *       400         *       420
GDC-1(full : SEINAQPAPVVENEVAKNRDNSPVITQAFFWPRVGEFLKKNDIVITETGTANFGIWDTKFPSGVTALSQV : 420
GDC-1_(23) : --------------------------FFWPRVGEFLKKNDIVITETGTANFGIWDTKFPSGVTALSQV :  42
GDC-1_(35) : SEINAQPAPVVENEVAKNRDNSPVITQAFFWPRVGEFLKKNDIVITETGTANFGIWDTKFPSGVTALSQV :  90
GDC-1_(59) : SEINAQPAPVVENEVAKNRDNSPVITQAFFWPRVGEFLKKNDIVITETGTANFGIWDTKFPSGVTALSQV : 303

*       440         *       460         *       480         *
GDC-1(full : LWGSIGWSVGACQGAVLAAADDNSDRRTILFVGDGSFQLTAQELSTMIRLKLKPIIFVICNDGFTIERFI : 490
GDC-1_(23) : LWGSIGWSVGACQGAVLAAADDNSDRRTILFVGDGSFQLTAQELSTMIRLKLKPIIFVICNDGFTIERFI : 112
GDC-1_(35) : LWGSIGWSVGACQGAVLAAADDNSDRRTILFVGDGSFQLTAQELSTMIRLKLKPIIFVICNDGFTIERFI : 160
GDC-1_(59) : LWGSIGWSVGACQGAVLAAADDNSDRRTILFVGDGSFQLTAQELSTMIRLKLKPIIFVICNDGFTIERFI : 373

500         *       520         *       540         *       560
GDC-1(full : HGMEAEYNDIANWDFKALVDVFGGSKTAKKFAVKTKDELDSLLTDPTFNAAECLQFVELYMPKEDAPRAL : 560
GDC-1_(23) : HGMEAEYNDIANWDFKALVDVFGGSKTAKKFAVKTKDELDSLLTDPTFNAAECLQFVELYMPKEDAPRAL : 182
GDC-1_(35) : HGMEAEYNDIANWDFKALVDVFGGSKTAKKFAVKTKDELDSLLTDPTFNAAECLQFVELYMPKEDA---- : 226
GDC-1_(59) : HGMEAEYNDIANWDFKALVDVFGGSKTAKKFAVKTKDELDSLLTDPTFNAAECLQFVELYMPKEDAPRAL : 443

*
GDC-1(full : IMTAEASARNNAKTE : 575
GDC-1_(23) : IMTAEASARNNAKTE : 197
GDC-1_(35) : --------------- :   -
GDC-1_(59) : IMTAEASARNNAKTE : 458
```

FIG. 2

```
                    *         20         *         40         *         60         *
GDC-1(full)      : MASINIRVQNLEQPMDVAEYLFRRLHEIGIRSIHGLPGDYNPLALDYLPSCG-LRWVGSVNELNAAYAADGYARV  :  74
A_oryzae-PDC     : --------MSLSTSSGDFVRLAFVQYTVFLVSINAPAWDYNLVALDYLPKCD-LHWVGNCNELNAGYAADGYARI  :  66
E._nidulans_PDC  : --MADIATRDVRQPIDIAEYLFRRLHEVGIRSVHGVPGDYNLAALDYLPKCG-LHWVGNCNELNAGYAADGYARV  :  72
S.cer_PDC1       : -----------MSEITLGKYLFERLKQVNVNTVFGLPGDFNLSLLDKIYEVEGMRWAGNANELNAAYAADGYARI  :  64
S.cer_PDC5       : -----------MSEITLGKYLFERLSQVNCNTVFGLPGDFNLSLLDKLYEVKGMRWAGNANELNAAYAADGYARI  :  64

80         *        100         *        120         *        140         *
GDC-1(full)      : KQMGALITTFGVGELSAINGVAGAFSEHVPVVHIVGCPSTASQRNGMLLHHTLGNGDFNIFANMSAQISCEVAKL  : 149
A_oryzae-PDC     : NGMSALVTTFGVGELSALNAIAGAYSEFVPIVHIVGQPHTKSQKDGMLLHHTLGNGDFNVFTRMSADISCTLGCL  : 141
E._nidulans_PDC  : NGIAALVTTFGVGELSAINAIAGRYSEFVPIIHIVGQPHSRSQKDGLLLHHTLGNGDYNVFSSMNKGISVTTANL  : 147
S.cer_PDC1       : KGMSCIITTFGVGELSALNGIAGSYAEHVGVLHVVGVPSISAQAKQLLLHHTLGNGDFTVFHRMSANISETTAMI  : 139
S.cer_PDC5       : KGMSCIITTFGVGELSALNGIAGSYAEHVGVLHVVGVPSISSQAKQLLLHHTLGNGDFTVFHRMSANISETTAMI  : 139

160         *        180         *        200         *        220
GDC-1(full)      : TNPAEIATQIDHALRVCFIRSRPVYIMLPTDMVQAKVEGARLKEPIDLSEPPNDPEKEAYVVDVVLKYLRA--AK  : 222
A_oryzae-PDC     : NSTHEVATLIDNAIRECWIRSRPVYISLPTDMVTKKIEGERLDTPLDLSLPPNDPEKEDYVVDVVLKYLHA--AK  : 214
E._nidulans_PDC  : NDTYDAATLIDNAIRECWIHSRPVYLALPTDMITKKIEGERLKTPIDLSLPANDPEKEDYVLVDARAQVFARSAK  : 222
S.cer_PDC1       : TDIATAPAEIDRCIRTTYVTQRPVYLGLPANLVDLNVPAKLLQTPIDMSLKPNDAESEKEVIDTILALVKD--AK  : 212
S.cer_PDC5       : TDIANAPAEIDRCIRTTYTTQRPVYLGLPANLVDLNVPAKLLETPIDLSLKPNDAEAEAEVVRTVVELIKD--AK  : 212

*        240         *        260         *        280         *        300
GDC-1(full)      : NPVILVDACAIRHR----VLDEVHDLIEKTNLPVFVTPMGKGAVNEEHPTYGGVYAGDGSHPPQVKDMVESSDLI  : 293
A_oryzae-PDC     : KPVILVDACAIRHR----VLDEVHEFVEKSGLPTFVAPMGKGAVDETHKNYGGVYAGTGSNP-GVREQVESSDLI  : 284
E._nidulans_PDC  : NPVILVDDSCVFDDSTGLSLEEVHDLIEVSGLPTFVAPMGKGAVNETHRCYGGVYAGTGSNP-GVREQVESSDLI  : 296
S.cer_PDC1       : NPVILADACCSRHD----VKAETKKLIDLTQFPAFVTPMGKGSIDEQHPRYGGVYVGTLSKP-EVKEAVESADLI  : 282
S.cer_PDC5       : NPVILADACASRHD----VKAETKKLMDLTQFPVYVTPMGKGAIDEQHPRYGGVYVGTLSRP-EVKKAVESADLI  : 282

*        320         *        340         *        360         *
GDC-1(full)      : LTIGALKSDFNTAGFSYRTSQLNTIDLHSDHCIVKYSTYPGVQMRGVLRQVIKQLDASEINAQPAPV-VENEVAK  : 367
A_oryzae-PDC     : LSIGAIKSDFNTTGFSYRIGQLNTIDFHSTYVRVRYSEYPDINMKGVLQKIVQRMGNLNVGPVSPPS-NLLPDNE  : 358
E._nidulans_PDC  : LSIGAIKSDFNTAGFSYRIGQLNTIDFHTTYVRVRYSEYPDTNMKGVLRKVIQRLGFIKADPVPHIS-NALPEHE  : 370
S.cer_PDC1       : LSVGALLSDFNTGSFSYSYKTKNIVEFHSDHMKIRNATFPGVQMKFVLQKLLTTIADAAKGYKPVAVPARTPANA  : 357
S.cer_PDC5       : LSIGALLSDFNTGSFSYSYKTKNIVEFHSDHIKIRNATFPGVQMKFALQKLLDAIPEVVKDYKPVAVPARVPITK  : 357

380         *        400         *        420         *        440         *
GDC-1(full)      : NRDNSPVITQAFFWPRVGEFLKKNDIVITETGTANFGIWDTKFPSGVTALSQVLWGSIGWSVGACQGAVLAAADD  : 442
A_oryzae-PDC     : KASTEQAITHAWLWPTVGQWLKEKDVVITETGTANFGIWDTRFPAGVTAISQVLWGSIGYSVGACQGAALAAKEQ  : 433
E._nidulans_PDC  : KNSSEQRITHAWMWPMVGQWLKENDIVITETGTANFGICWNLLPSELQPISQVLWGSIGYSVGACQGAALAAKEQ  : 445
S.cer_PDC1       : AVPASTPLKQEWMWNQLGNFLQEGDVVIAETGTSAFGINQTTFPNNTYGISQVLWGSIGFTTGATLGAAFAAEEI  : 432
S.cer_PDC5       : STPANTPMKQEWMWNQLGNFLREGDIVIAETGTSAFGINQTTFPTDVYAIVQVLWGSIGFTVGALLGATMAAEEL  : 432

460         *        480         *        500         *        520
GDC-1(full)      : NSDRRTILFVGDGSFQLTAQELSTMIRLKLKPIIFVICNDGFTIERFIHGMEAEYNDIANWDFKALVDVFGGSKT  : 517
A_oryzae-PDC     : G--RRTVLFVGDGSFQLTLQEVSTMIRNNLNPIIFVICNEGYTIERYIHGWEAVYNDIQPWDFLNIPVAFGAKDK  : 506
E._nidulans_PDC  : GN-RRTVLFVGDGSLQLTLQEISTMIRWGLKPIIFVICCGEGYTIERFIHGWDESYNDIQTWDIKGLPVAFGGKGR  : 519
S.cer_PDC1       : DPKKRVILFIGDGSLQLTVQEISTMIRWGLKPYLFVLNNDGYTIEKLIHGPKAQYNEIQGWDHLSLLPTFGAKD-  : 506
S.cer_PDC5       : DPKKRVILFIGDGSLQLTVQEISTMIRWGLKPYIFVLNNNGYTIEKLIHGPHAEYNEIQGWDHLALLPTFGARN-  : 506

540         *        560         *        580
GDC-1(full)      : AKKFAVKTKDELDSLLTDPTFNAAECLQFVELYMPKEDAPRALIMTAEASARNNAKTE        : 575
A_oryzae-PDC     : YKGYKVTTRDELRELFANEEFASAPCLQFEIDSRGIR---------------------        : 543
E._nidulans_PDC  : YKGYKVTTRDELTKLFASEEFSSTPCLQVSLCDLTHYLSDANFEQLG-----------        : 566
S.cer_PDC1       : YETHRVATTGEWDKLTQDKSFNDNSKIRMIEIMLPVFDAPQNLVEQAKLTAATNAKQ-        : 563
S.cer_PDC5       : YETHRVATTGEWEKLTQDKDFQDNSKIRMIEVMLPVFDAPQNLVKQAQLTAATNAKQ-        : 563
```

FIG. 3

GDC-1 GENES CONFERRING HERBICIDE RESISTANCE

CROSS-REFERENCE TO RELATED APPLICATIONS

This application is a continuation-in-part of copending U.S. patent application Ser. No. 10/796,953, filed Mar. 10, 2004, which claims the benefit of U.S. Provisional Application Ser. No. 60/453,237, filed Mar. 10, 2003, each of which is hereby incorporated in its entirety by reference herein.

FIELD OF THE INVENTION

This invention provides novel genes encoding herbicide resistance, which are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phosphoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases may have a high tolerance to glyphosate.

Plant cells resistant to glyphosate toxicity can be produced by transforming plant cells to express glyphosate-resistant EPSP synthases. A mutated EPSP synthase from *Salmonella typhimurium* strain CT7 confers glyphosate resistance in bacterial cells, and confers glyphosate resistance on plant cells (U.S. Pat. Nos. 4,535,060, 4,769,061, and 5,094,945). Thus, there is a precedent for use of glyphosate-resistant bacterial EPSP synthases to confer glyphosate resistance upon plant cells.

An alternative method to generate target genes resistant to a toxin (such as an herbicide) is to identify and develop enzymes that result in detoxification of the toxin to an inactive or less active form. This can be accomplished by identifying enzymes that encode resistance to the toxin in a toxin-sensitive test organism, such as a bacterium.

Castle et al (WO 02/36782 A2) describe proteins (glyphosate N-acetyltransferases) that are described as modifying glyphosate by acetylation of a secondary amine to yield N-acetylglyphosate.

Barry et al (U.S. Pat. No. 5,463,175) describes genes encoding an oxidoreductase (GOX), and states that GOX proteins degrade glyphosate by removing the phosphonate residue to yield amino methyl phosphonic acid (AMPA). This suggests that glyphosate resistance can also be conferred, at least partially, by removal of the phosphonate group from glyphosate. However, the resulting compound (AMPA) appears to provide reduced but measurable toxicity upon plant cells. Barry describes the effect of AMPA accumulation on plant cells as resulting in effects including chlorosis of leaves, infertility, stunted growth, and death. Barry (U.S. Pat. No. 6,448,476) describes plant cells expressing an AMPA-N-acetyltransferase (phnO) to detoxify AMPA.

Phophonates, such as glyphosate, can also be degraded by cleavage of C—P bond by a C—P lyase. Wacket et al. (1987) *J. Bacteriol.* 169:710-717 described strains that utilize glyphosate as a sole phosphate source. Kishore et al. (1987) *J. Biol. Chem.* 262:12164-12168 and Shinabarger et al. (1986) *J. Bacteriol.* 168:702-707 describe degradation of glyphosate by C—P Lyase to yield glycine and inorganic phosphate.

While several strategies are available for detoxification of toxins, such as the herbicide glyphosate, as described above, new activities capable of degrading glyphosate are useful. Novel genes and genes conferring glyphosate resistance by novel mechanisms of action would be of additional usefulness. Single genes conferring glyphosate resistance by formation of non-toxic products would be especially useful.

Thus, novel genes encoding resistance to herbicides are needed.

SUMMARY OF INVENTION

Compositions and methods for conferring herbicide resistance to plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed plants, plant cells, tissues, and seeds.

In particular, isolated nucleic acid molecules corresponding to glyphosate resistance-conferring nucleic acid sequences are provided. Additionally, amino acid sequences corresponding to the polynucleotides are encompassed. In particular, the present invention provides for isolated nucleic acid molecules comprising nucleotide sequences encoding an amino acid sequence shown in SEQ ID NO:3, 6, 8, 11, 19, or 21, or a nucleotide sequence set forth in SEQ ID NO:1, 2, 4, 5, 7, 9, 10, 18, or 20, as well as variants and fragments thereof. Nucleotide sequences that are complementary to a nucleotide sequence of the invention, or that hybridize to a sequence of the invention are also encompassed.

DESCRIPTION OF FIGURES

FIG. 2 shows an alignment of the predicted proteins resulting from translation of the clones GDC-1 (full) (SEQ ID NO:19), GDC-1 (23) (SEQ ID NO:6), GDC-1 (35) (SEQ ID NO:8), and GDC-1 (59) (SEQ ID NO:11).

FIG. 3 shows an alignment of GDC-1 protein (SEQ ID NO:19) to pyruvate decarboxylase of *Saccharomyces cerevesiae* (SEQ ID NO:13), a putative indole-3-pyruvate decarboxylase from *Salmonella typhimurium* (SEQ ID NO:14), pyruvate decarboxylase (EC 4.1.1.1) from *Zymomonas mobilis* (SEQ ID NO:15), acetolactate synthase from *Saccharomyces cerevesiae* (SEQ ID NO:16), and acetolactate synthase from *Magnaporthe grisea* (SEQ ID NO:17). The alignment shows the most highly conserved amino acid residues highlighted in black, and highly conserved amino acid residues highlighted in gray.

DETAILED DESCRIPTION

Figure 1:
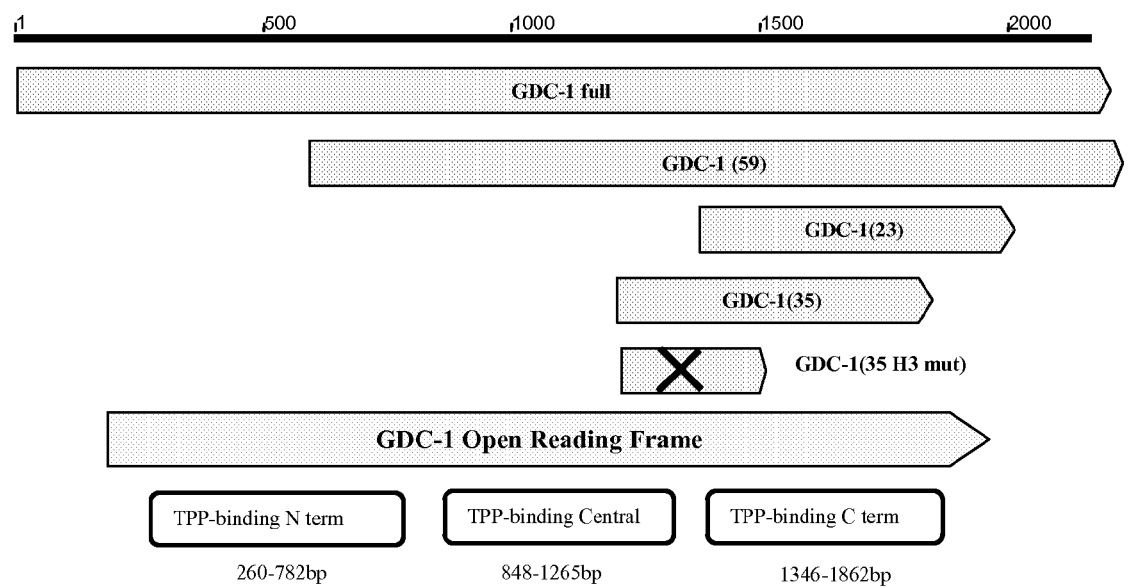
FIG. 1 is a diagram that shows GDC-1 (full), GDC-1 (23), GDC-1 (35), GDC-1 (59), and GDC-1 (35 H3mut), as well as the location of the TPP binding domains and the location (X) of a mutation.

The present invention is drawn to compositions and methods for regulating resistance in organisms, particularly in plants or plant cells. The methods involve transforming organisms with nucleotide sequences encoding a glyphosate resistance protein of the invention. In particular, the nucleotide sequences of the invention are useful for preparing plants that show increased tolerance to the herbicide glyphosate. Thus, transformed plants, plant cells, plant tissues and seeds are provided. Compositions include nucleic acids and proteins relating to glyphosate tolerance in plants as well as transformed plants, plant tissues and seeds. More particularly, nucleotide sequences encoding all or part of the "glyphosate resistance-conferring decarboxylase" gene GDC-1 and the amino acid sequences of the proteins encoded thereby are disclosed. The sequences find use in the construction of expression vectors for subsequent transformation into organisms of interest, as probes for the isolation of other glyphosate resistance genes, as selectable markers, and the like.

Definitions

"Glyphosate" includes any herbicidal form of N-phosphonomethylglycine (including any salt thereof) and other forms that result in the production of the glyphosate anion in planta.

"Glyphosate (or herbicide) resistance-conferring decarboxylase" or "GDC" includes a DNA segment that encodes all or part of a glyphosate (or herbicide) resistance protein. This includes DNA segments that are capable of expressing a protein that confers glyphosate (herbicide) resistance to a cell.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer time than cells that do not express the protein.

A "glyphosate resistance protein" includes a protein that confers upon a cell the ability to tolerate a higher concentration of glyphosate than cells that do not express the protein, or to tolerate a certain concentration of glyphosate for a longer time than cells that do not express the protein. By "tolerate" or "tolerance" is intended either to survive, or to carry out essential cellular functions, such as protein synthesis and respiration, in a manner that is not readily discernable from untreated cells.

By "decarboxylase" is intended a protein, or a gene encoding a protein, whose catalytic mechanism can include cleavage and release of a carboxylic acid. This includes enzymes that liberate $CO_2$, such as pyruvate decarboxlyases, acetolactate synthases, and orthinine decarboxylases, as well as enzymes that liberate larger carboxylic acids. "Decarboxylase" includes proteins that utilize thiamine pyrophoshate as a cofactor in enzymatic catalysis. Many such decarbolyases also utilize other cofactors, such as FAD.

By "TPP-binding domain" is intended a region of conserved amino acids present in enzymes that are capable of utilizing TPP as a cofactor.

"Plant tissue" includes all known forms of plants, including undifferentiated tissue (e.g. callus), suspension culture cells, protoplasts, plant cells including leaf cells, root cells and phloem cells, plant seeds, pollen, propagules, embryos and the like.

"Plant expression cassette" includes DNA constructs that are capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

"Signal sequence" includes sequences that are known or suspected to result in cotranslational or post-translational peptide transport across the cell membrane. In eukaryotes, this typically involves secretion into the Golgi apparatus, with some resulting glycosylation.

"Leader sequence" includes any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

"Plant transformation vector" includes DNA molecules that are necessary for efficient transformation of a plant cell. Such a molecule may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451).

"Vector" refers to a nucleic acid construct designed for transfer between different host cells. "Expression vector" refers to a vector that has the ability to incorporate, integrate and express heterologous DNA sequences or fragments in a foreign cell.

"Transgenic plants" or "transformed plants" or "stably transformed plants or cells or tissues" refers to plants that have incorporated or integrated exogenous or endogenous nucleic acid sequences or DNA fragments or chimeric nucleic acid sequences or fragments.

"Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Provided here is a novel isolated gene that confers resistance to glyphosate. Also provided are amino acid sequences of the GDC-1 protein. The protein resulting from translation of this gene allows cells to function in the presence of concentrations of glyphosate that are otherwise toxic to cells, including plant cells and bacterial cells.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. A glyphosate resistance protein that is substantially free of cellular material includes preparations of protein having less than about 30%, 20%, 10%, or 5% (by dry weight) of non-glyphosate resistance protein (also referred to herein as a "contaminating protein"). Various aspects of the invention are described in further detail in the following subsections.

Isolated Nucleic Acid Molecules, and Variants and Fragments Thereof

One aspect of the invention pertains to isolated nucleic acid molecules comprising nucleotide sequences encoding glyphosate resistance proteins and polypeptides or biologically active portions thereof, as well as nucleic acid molecules sufficient for use as hybridization probes to identify glyphosate resistance-encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS:1, 2, 18, and 20, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the glyphosate resistance proteins encoded by the nucleotide sequences are set forth in SEQ ID NOS:3, 19, and 21. The invention also encompasses nucleic acid molecules comprising nucleotide sequences encoding partial-length glyphosate resistance proteins, including the sequences set forth in SEQ ID NOS:4, 5, 7, 9, and 10, and complements thereof. The corresponding amino acid sequences for the glyphosate resistance proteins encoded by these partial-length nucleotide sequences are set forth in SEQ ID NOS:6, 8, and 11.

Nucleic acid molecules that are fragments of these glyphosate resistance-encoding nucleotide sequences are also encompassed by the present invention. By "fragment" is intended a portion of the nucleotide sequence encoding a glyphosate resistance protein. A fragment of a nucleotide sequence may encode a biologically active portion of a glyphosate resistance protein, or it may be a fragment that can be used as a hybridization probe or PCR primer using methods disclosed below. Nucleic acid molecules that are fragments of a glyphosate resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200 nucleotides, or up to the number of nucleotides present in a full-length glyphosate resistance-encoding nucleotide sequence disclosed herein (for example, 2210 nucleotides for SEQ ID NO:1) depending upon the intended use.

Fragments of the nucleotide sequences of the present invention generally will encode protein fragments that retain the biological activity of the full-length glyphosate resistance protein; i.e., glyphosate resistance activity. By "retains glyphosate resistance activity" is intended that the fragment will have at least about 30%, preferably at least about 50%, more preferably at least about 70%, even more preferably at least about 80% of the glyphosate resistance activity of the full-length glyphosate resistance protein disclosed herein as SEQ ID NO:19. Methods for measuring glyphosate resistance activity are well known in the art. See, for example, U.S. Pat. Nos. 4,535,060, and 5,188,642, each of which are herein incorporated by reference in their entirety.

A fragment of a glyphosate resistance-encoding nucleotide sequence that encodes a biologically active portion of a protein of the invention will encode at least about 15, 25, 30, 50, 75, 100, 125, 150, 175, 200, 250, 300, 350, 400, 450, 500, or 550 contiguous amino acids, or up to the total number of amino acids present in a full-length glyphosate resistance protein of the invention (for example, 575 amino acids for SEQ ID NO:3).

Preferred glyphosate resistance proteins of the present invention are encoded by a nucleotide sequence sufficiently identical to the nucleotide sequence of SEQ ID NO:1, 2, 4, 5, 7, 9, 10, 18, or 20. The term "sufficiently identical is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to GDC-like nucleic acid molecules of the invention. BLAST protein searches can be performed with the BLASTX program, score=50, wordlength=3, to obtain amino acid sequences homologous to glyphosate resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) supra. GAP Version 10 may be used with the following parameters: % identity and % similarity for a nucleotide sequence using GAP Weight of 50 and Length Weight of 3, and the nwsgap-dna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The invention also encompasses variant nucleic acid molecules. "Variants" of the glyphosate resistance-encoding nucleotide sequences include those sequences that encode the glyphosate resistance proteins disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the glyphosate resistance proteins disclosed in the present invention as discussed below. Variant proteins encompassed by the present invention are biologically active, that is they retain the desired biological activity of the native protein, that is, glyphosate resistance activity. By "retains glyphosate resistance activity" is intended that the variant will have at least about 30%, preferably at least about 50%, more preferably at least about 70%, even more preferably at least about 80% of the glyphosate resistance activity of the native protein. Methods for measuring glyphosate resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded glyphosate resistance proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of a glyphosate resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in the alignment of FIG. 3. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer glyphosate resistance activity to identify mutants that retain activity. Following mutagenesis, the encoded protein can be expressed recombinantly, and the activity of the protein can be determined using standard assay techniques.

Using methods such as PCR, hybridization, and the like corresponding glyphosate resistance sequences can be identified, such sequences having substantial identity to the sequences of the invention. See, for example, Sambrook J., and Russell, D. W. (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the glyphosate resistance nucleotide sequence can be used to screen cDNA or genomic libraries. Methods for construction of such cDNA and genomic libraries are generally known in the art and are disclosed in Sambrook and Russell, 2001. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known glyphosate resistance-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of glyphosate resistance-encoding nucleotide sequence of the invention or a fragment or variant thereof. Preparation of probes for hybridization is generally known in the art and is disclosed in Sambrook and Russell, 2001 and Sambrook et al. (1989) *Molecular Cloning: A Laboratory Manual* (2d ed., Cold Spring Harbor Laboratory Press, Plainview, N.Y.), both of which are herein incorporated by reference.

For example, an entire glyphosate resistance sequence disclosed herein, or one or more portions thereof, may be used as a probe capable of specifically hybridizing to corresponding glyphosate resistance sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding glyphosate resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 110° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated Proteins and Variants and Fragments Thereof

Glyphosate resistance proteins are also encompassed within the present invention. By "glyphosate resistance protein" is intended a protein having the amino acid sequence set forth in SEQ ID NO:3, 19, or 21. Fragments, biologically active portions, and variants thereof are also provided, and may be used to practice the methods of the present invention.

"Fragments" or "biologically active portions" include polypeptide fragments comprising a portion of an amino acid sequence encoding a glyphosate resistance protein as set forth in SEQ ID NO:3, 19, or 21, and that retains glyphosate resistance activity. A biologically active portion of a glyphosate resistance protein can be a polypeptide that is, for example, 10, 25, 50, 100 or more amino acids in length. Such biologically active portions can be prepared by recombinant techniques and evaluated for glyphosate resistance activity. Methods for measuring glyphosate resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NO:3, 19, or 21. The invention encompasses other fragments, however, such as any fragment in the protein greater than about 10, 20, 30, 50, 100, 150, 200, 250, 300, 350, 400, 450, 500, 550, or 600 amino acids.

By "variants" is intended proteins or polypeptides having an amino acid sequence that is at least about 60%, 65%, preferably about 70%, 75%, more preferably, 80%, 85%, most preferably 90%, 91%, 92%, 93%, 94%, 95%, 96%, 97%, 98% or 99% identical to the amino acid sequence of SEQ ID NO:3, 6, 8, 11, 19, or 21. Variants also include polypeptides encoded by a nucleic acid molecule that hybridizes to the nucleic acid molecule of SEQ ID NO:1, 2, 4, 5, 7, 9, 10, 18, or 21, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining glyphosate resistance activity. Methods for measuring glyphosate resistance activity are well known in the art. See, for example, U.S. Pat. Nos. 4,535,060, and 5,188,642, each of which are herein incorporated by reference in their entirety.

Altered or Improved Variants

It is recognized that DNA sequences of GDC-1 may be altered by various methods, and that these alterations may result in DNA sequences encoding proteins with amino acid sequences different than that encoded by GDC-1. This protein may be altered in various ways including amino acid substitutions, deletions, truncations, and insertions. Methods for such manipulations are generally known in the art. For example, amino acid sequence variants of the GDC-1 protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired glyphosate resistance activity. However, it is understood that the ability of GDC-1 to confer glyphosate resistance may be improved by the use of such techniques upon the compositions of this invention. For example, one may express GDC-1 in host cells that exhibit high rates of base misincorporation during DNA replication, such as XL-1 Red (Stratagene). After propagation in such strains, one can isolate the GDC-1 DNA (for example by preparing plasmid DNA, or by amplifying by PCR and cloning the resulting PCR fragment into a vector), culture the GDC-1 mutations in a non-mutagenic strain, and identify mutated GDC-1 genes with improved resistance to glyphosate, for example by growing cells in increasing concentrations of glyphosate and testing for clones that confer ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different glyphosate resistance protein coding regions can be used to create a new glyphosate resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the glyphosate resistance gene of the invention and other known glyphosate resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Transformation of Bacterial or Plant Cells

In one aspect of the invention, the GDC-1 gene is useful as a marker to assess transformation of bacterial or plant cells. Transformation of bacterial cells is accomplished by one of several techniques known in the art, not limited to electroporation, or chemical transformation (See for example Ausubel (ed.), Current Protocols in Molecular Biology, John Wiley and Sons, Inc. (1994)). Markers conferring resistance to toxic substances are useful in identifying transformed cells (having taken up and expressed the test DNA) from non-transformed cells (those not containing or not expressing the test DNA). By engineering GDC-1 to be (1) expressed from a bacterial promoter known to stimulate transcription in the organism to be tested, (2) properly translated to generate an intact GDC-1 peptide, and (3) placing the cells in an otherwise toxic concentration of glyphosate, one can identify cells that have been transformed with DNA by virtue of their resistance to glyphosate.

Transformation of plant cells can be accomplished in similar fashion. First, one engineers the GDC-1 gene in a way that allows its expression in plant cells. The glyphosate resistance sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes. The organization of such constructs is well known in the art.

Such an expression cassette is provided with a plurality of restriction sites for insertion of the glyphosate resistance sequence to be under the transcriptional regulation of the regulatory regions. The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably-linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression. In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc. Many types of vectors can be used to transform plant cells for achieving glyphosate resistance.

In general, plant transformation methods involve transferring heterologous DNA into target plant cells (e.g. immature or mature embryos, suspension cultures, undifferentiated callus, protoplasts, etc.), followed by applying a maximum threshold level of appropropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation). Bombardment of plant cells with heterologous foreign DNA adhered to particles including aerosol beam transformation (U.S. Published Application No. 20010026941; U.S. Pat. No. 4,945,050; International Publication No. WO 91/00915; U.S. Published Application No. 2002015066), and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Following integration of heterologous foreign DNA into plant cells, one then applies a maximum threshold level of glyphosate in the medium to kill the untransformed cells and separate and proliferate the putatively transformed cells that survive from this selection treatment by transferring regularly to a fresh medium. By continuous passage and challenge with glyphosate, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001). PCR is carried out using oligonucleotide primers specific to the gene of interest or *Agrobacterium* vector background, etc.

Southern Analysis: Plant transformation is confirmed by Southern blot analysis of genomic DNA (Sambrook and Russell, 2001). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}P$ target DNA fragment to confirm the integration of introduced gene in the plant genome according to standard techniques (Sambrook and Russell, 2001. *Molecular Cloning: A Laboratory Manual*. Cold Spring Harbor Laboratory Press, Cold Spring Harbor, N.Y.

Northern Analysis: RNA is isolated from specific tissues of transformant, fractionated in a formaldehyde agarose gel, blotted onto a nylon filter according to standard procedures that are routinely used in the art (Sambrook, J., and Russell, D. W. 2001. *Molecular Cloning: A Laboratory Manual*, Cold Spring Harbor Laboratory Press, Cold Spring Harbor, N.Y.). Expression of RNA encoded by GDC-1 is then tested by hybridizing the filter to a radioactive probe derived from a GDC, by methods known in the art (Sambrook and Russell, 2001)

Western blot and Biochemical assays: Western blot and biochemical assays and the like may be carried out on the transgenic plants to determine the presence of protein encoded by the glyphosate resistance gene by standard procedures (Sambrook, J., and Russell, D. W. 2001. *Molecular Cloning: A Laboratory Manual*, Cold Spring Harbor Laboratory Press, Cold Spring Harbor, N.Y.) using antibodies that bind to one or more epitopes present on the glyphosate resistance protein.

Transgenic Plants

In another aspect of the invention, one may generate transgenic plants expressing GDC-1 that are more resistant to high concentrations of glyphosate than non-transformed plants. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing GDC-1 may be isolated by common methods described in the art, for example by transformation of callus, selection of transformed callus, and regeneration of fertile plants from such transgenic callus. In such process, GDC-1 may be used as selectable marker. Alternatively, one may use any gene as a selectable marker so long as its expression in plant cells confers ability to identify or select for transformed cells. Genes known to function effectively as selectable markers in plant transformation are well known in the art.

The following examples are offered by way of illustration and not by way of limitation.

EXPERIMENTAL

Example 1

Isolation of ATX6394

Glyphosate-resistant fungi were isolated by plating samples of soil on Enriched Minimal Media (EMM) containing glyphosate as the sole source of phosphorus. Since EMM contains no aromatic amino acids, a strain must be resistant to glyphosate in order to grow on this media.

Two grams of soil was suspended in approximately 30 ml of water, and sonicated for 30 seconds in an Aquasonic sonicator water bath. The sample was vortexed for 5 seconds and permitted to settle for 60 seconds. This process was repeated 3 times. 100 µl of this suspension was added to 2 ml of Enriched Minimal Media II (EMM II) supplemented with 4 mM glyphosate (pH 6.0) EMMII contains Solution A (In 900 mls: 10 g sucrose (or other carbon source), 2 g $NaNO_3$, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl)) and Solution B (In 100 mls: 0.21 g $Na_2HPO_4$, 0.09 g $NaH_2PO_4$, pH 7.0). The culture was shaken on a tissue culture roller drum for eight days at 21° C. and then transferred into 2 ml of fresh EMMII containing 4 mM glyphosate as the only phosphorus source. After five days, the culture was plated onto solid media by streaking a 1 µl loop onto the surface of agar plate containing EMMII agar containing 5 mM glyphosate as the sole phosphorus source. The plate was sealed with parafilm and incubated until suitable growth was attained. Fresh plates were inoculated by agar plugs to isolate the fungus into pure culture.

One particular strain, designated ATX6394, was selected due to its ability to grow in the presence of high glyphosate concentrations.

Example 2

Construction of cDNA Library from Strain ATX6394

ATX6394 was grown in (liquid media L+phosphorous) containing 5 mM glyphosate, and total RNA was isolated using Trizol reagent (Invitrogen). poly(A)+ mRNA was isolated from total RNA using Poly(A) Purist mRNA Purification kit (Ambion). cDNA was synthesized from polyA+ mRNA using ZAP cDNA Synthesis kit from Stratagene, and cloned into the lambda Zap II expression vector (Stratagene).

Example 3

In vivo Excision of cDNA Clones

The ATX6394 cDNA library was excised in bulk as per manufacturers protocol (Stratagene), transfected into the SOLR strain of *E. coli* (Stratagene), plated directly onto M9 minimal media plates containing thiamine, proline, ampicillin and 5 mM glyphosate and incubated at 37° C. (M9 media contains 30 g $Na_2HPO_4$, 15 g $KH_2PO_4$, 5 g $NH_4Cl$, 2.5 g NaCl, and 15 mg $CaCl_2$).

Example 4

Identification of cDNA Clones Conferring Glyphosate Resistance in *E. coli*

Following 2 days growth, 51 colonies had grown in the presence of 5 mM glyphosate, and these clones were selected for further study. Plasmid DNA from 48 of the 51 positive clones was isolated and transformed into the alternate host strain XL-1 Blue MRF' (Stratagene) and plasmid DNA was prepared for sequencing.

We determined the DNA sequence of 48 clones conferring glyphosate resistance (5 mM). Three clones (#23, 35, 59) were found to represent the same open reading frame. Therefore we designated this open reading frame GDC-1. The nucleotide sequences of clones #23, 35, and 59 are provided in SEQ ID NOS:4, 7, and 9 respectively.

Example 5

Isolation of Full-Length GDC-1 Construct (GDC-1 (Full))

Comparison of GDC-1 (29) GDC-1 (35) and GDC-1 (59) suggested that these clones did not represent the entire cDNA for the GDC-1 mRNA. To generate a full length GDC-1 clone, we performed 5' RACE using the SMART RACE cDNA Amplification kit (BD Biosciences) to amplify the 5' end of the GDC-1 from ATX6394 poly(A)+ mRNA. Oligo [SMARTgrg3.rev 5'TCCCAGATGCCAAAGTTGGCTGT-TCCAGTC 3']; SEQ ID NO:12 was derived from the sequence of GDC-1 (#35). We cut the resultant PCR product with HindIII and ligated this to the existing GDC-1 (59) cDNA in pBluescript to generate the full length cDNA, referred to herein as GDC-1 (full). The DNA sequence of GDC-1 (full) was determined, and found to contain a complete protein-coding region. This coding region is referred to herein as GDC-1. Amino acid sequences resulting from the translation of the GDC-1 gene are provided in SEQ ID NOS: 3, 19, and 21.

GDC-1 (59) consists of amino acid residues 118 to 575 of GDC-1 (full) (SEQ ID NO:19). GDC-1 (35) consists of amino acid residues 331 to 556 of GDC-1 (full) (SEQ ID NO:19). GDC-1 (23) consists of amino acid residues 379 to 575 of GDC-1 (full) (SEQ ID NO:19).

Example 6

Disruption of GDC-1 ORF Eliminates Glyphosate Resistance

To confirm that GDC-1 ORF is responsible for conferring glyphosate resistance, we engineered a mutant of GDC-1 (35), and tested its ability to confer glyphosate resistance. The GDC-1 (35) construct contains a single recognition site for HindIII restriction enzyme. GDC-1 (35) was digested with the restriction enzyme Hind III, and the resulting recessed 3' ends extended by incubating with T4 DNA polymerase and dNTPs, as known in the art (Sambrook). The resulting molecules were then religated using T4 DNA ligase (Maniatis). The religated molecules were identified by min-prep of transformed clones, and the DNA was sequenced. The resulting clone, GDC-1 (35-H3mut), contains a four nucleotide insertion in the GDC-1 open reading frame. This four nucleotide insertion leads to the premature termination of translation of the GDC-1 (35) protein at a premature stop codon at nucleotides 1451-1453 of GDC-1 full length sequence.

TABLE 1

Glyphosate resistance of GDC-1(35) and the mutant GDC-1 (35-H3mut)

|  | M9 media + Amp + 10 mM Glyphosate |
|---|---|
| Vector (pBluescript SK+) | − |
| GDC-1(35) | +++ |
| GDC-1(35-H3mut) | − |

Example 7

GDC-1 Does Not Complement an aroA Mutation in E. coli

The *E. coli* aroA gene codes for EPSP synthase, the target enzyme for glyphosate. EPSP synthase catalyzes the sixth step in the biosynthesis of aromatic amino acids in microbes and plants. aroA mutants that lack an EPSP synthase do not grow on minimal media that lacks aromatic amino acids (Pittard and Wallace (1966) *J. Bacteriol.* 91:1494-508), but can grow in rich media, such as LB. However, genes encoding EPSPS activity can restore the ability to grow on glyphosate upon aroA mutant *E. coli* strains. Thus, a test for genetic complementation of an aroA mutant is a highly sensitive method to test if a gene is capable of functioning as an EPSPS in *E. coli*. Such tests for gene function by genetic complementation are known in the art.

A deletion of the aroA gene was created in *E. coli* XL-1 MRF' (Stratagene) by PCR/recombination methods known in the art and outlined by Datsenko and Wanner, (2000) *Proc. Natl. Acad. Sci. USA* 97:6640-6645. This system is based on the Red system that allows for chromosomal disruptions of targeted sequences. A large portion (1067 nt of the 1283 nt) of the aroA coding region was disrupted by the engineered deletion. The presence of the deletion was confirmed by PCR with several sets of oligonucleotides, and by the appearance of an aroA phenotype in the strain, referred to herein as 'ΔaroA'. ΔaroA grows on LB media (which contains all amino acids) and grows on M63 media supplemented with phenylalanine, tryptophan, and tyrosine, but does not grow on M63 minimal media (which lacks aromatic amino acids). These results indicate that ΔaroA exhibits an aroA phenotype.

The ability of an EPSPS to complement the mutant phenotype of ΔaroA was confirmed. Clone pAX482, an *E. coli* expression vector containing the wild-type *E. coli* aroA gene, was transformed into ΔaroA, and transformed cells were selected. These cells (containing a functional aroA gene residing on a plasmid) were then plated on LB media, M63, and M63 with amino acid supplements. Where the ΔaroA mutant strain grew only on LB and M63 supplemented with aromatic amino acids, ΔaroA cells containing the functional aroA gene on a plasmid grew on all three media types.

In order to determine whether or not GDC-1 could confer complementation, plasmid pAX472, the expression vector containing GDC-1, was transformed into ΔaroA and plated on the same three types of media. Cells transformed with pAX472 were able to grow on M63 media supplemented with phenylalanine, tryptophan, and tyrosine and LB media but they were not able to grow on M63 alone. Thus, GDC-1 was not capable of complementing the aroA mutation, and thus GDC-1 is not EPSP synthase.

Example 8

GDC-1 is a TPP-Binding Decarboxylase

The predicted amino acid sequence of GDC-1 was compared to the non-redundant database of sequences maintained by the National Center for Biotechnology Information (NCBI), using the BLAST2 algorithm (Altschul et al. (1990) *J. Mol. Biol.* 215:403-410; Altschul et al. (1997) *Nucleic Acids Res.* 25:3389-3402; Gish and States (1993) *Nature Genet.* 3:266-272). Comparison of GDC-1 with public DNA and amino acid databases, such as the non-redundant database of GenBank, the Swissprot database, and the 'pat' database of GenBank show that GDC-1 encodes a novel protein. Results from a BLAST search of the NCBI nr database are shown in Table 2. The sequences obtained using the Genbank Accession Nos. provided are herein incorporated by reference in their entirety. The results of BLAST searches identified homology between the predicted GDC-1 open reading frame (SEQ ID NO:3) and several known proteins. The highest scoring amino acid sequences from this search were aligned with GDC-1 using ClustalW algorithm (Higgins et al. (1994) *Nucleic Acids Res.* 22:4673-4680) [as incorporated into the program ALIGNX module of the vector NTi Program Suite, Informax, Inc.]. After alignment with ClustalW, the percent amino acid identity was assessed. The protein encoded by GDC-1 has homology to several members of the fungal pyruvate decarboxylase enzyme family. The highest protein homology identified is the *Aspergillus oryzae* pyruvate decarboxylase (pdcA) gene. GDC-1 also shares homology with indole-3 pyruvate decarboxylases, found in bacteria such as *Salmonella typhimurium*. A similar search of the patent database at NCBI also identifies proteins with homology to GDC-1, though proteins identified in this search are less related to GDC-1. The percent amino acid identity of GDC-1 with members of these protein classes is shown in Table 3.

Further analysis of GDC-1 sequence shows that GDC-1 contains conserved domains characteristic of proteins that utilize Thiamine Pyrophosphate (TPP) as a cofactor. These domains are collectively and singly referred to as a "TPP binding domain". Analysis of GDC-1 sequence shows that amino acids 13-187 of SEQ ID NOS:3, 19, and 21 constitute an N-terminal domain of TPP-binding domain, amino acids 375-547 of SEQ ID NOS:3, 19, and 21 constitute a central domain of TPP-binding domain, and amino acids 209-348 of SEQ ID NOS:3, 19, and 21 constitute a C-terminal domain of TPP-binding domain. It is understood that these amino acid coordinates are only approximations of the location of such domains as judged by homology with known TPP binding proteins, and are not limiting to the invention. An alignment of GDC-1 with other known TPP-binding proteins is shown in FIG. 3.

TABLE 2

High scoring open reading frames from BLAST search of NCBI nr database

| Genbank Accession No. | Organism | Gene Description |
| --- | --- | --- |
| gi\|4323052\|gb\|AF098293.1\|AF098293 | *Aspergillus oryzae* | pyruvate decarboxylase (pdcA) |
| gi\|2160687\|gb\|U73194.1\|ENU73194 | *Emericella nidulans* | pyruvate decarboxylase (pdcA) |

TABLE 2-continued

High scoring open reading frames from BLAST search of NCBI nr database

| Genbank Accession No. | Organism | Gene Description |
|---|---|---|
| gi\|25992751\|gb\|AF545432.1\| | *Candida glabrata* | pyruvate decarboxylase (PDC) |
| gi\|4115\|emb\|X55905.1\|SCPDC6 | *Saccharomyces cerivisiae* | PDC6 gene for pyruvate decarboxylase |
| gi\|173308\|gb\|L09727.1\|YSKPDC1A | *Kluyveromyces marxianus* | pyruvate decarboxylase (PDC1) |
| gi\|535343\|gb\|U13635.1\|HUU13635 | *Hanseniaspora uvarum* | pyruvate decarboxylase (PDC) |
| gi\|4113\|emb\|X15668.1\|SCPDC5 | *Saccharomyces cerivisiae* | PDC5 gene for pyruvate decarboxylase (EC4.1.1.1.) |
| gi\|452688\|emb\|X77316.1\|SCPDC1A | *Saccharomyces cerivisiae* | PDC1 |

TABLE 3

Percent identity of GDC-1 to related proteins from various fungi and bacteria

| Organism | Gene Product | % amino acid identity |
|---|---|---|
| *Aspergillus oryzae* | Pyruvate decarboxylase | 58% |
| *Emericalla nidulans* | Pyruvate decarboxylase | 56% |
| *Candida glabrata* | Pyruvate decarboxylase | 49% |
| *Kluyveromyces marxianus* | Pyruvate decarboxylase | 47% |
| *Saccharomyces cerevisiae* | Pyruvate decarboxylase PDC1 | 46% |
| *Saccharomyces cerevisiae* | Pyruvate decarboxylase PDC5 | 47% |
| *Saccharomyces cerevisiae* | Pyruvate decarboxylase PDC6 | 47% |
| *Pichia Stipitis* | Pyruvate decarboxylase PDC2 | 45% |
| *Salmonella typhimurium* | Indole-3 pyruvate decarboxylase | 33% |
| *Neurospora crassa* | Pyruvate decarboxylase | 28% |
| *Nicotiana tabacum* | Pyruvate decarboxylase | 28% |
| *Zymomonas mobilis* | Pyruvate decarboxylase | 27% |

Example 9

Engineering GDC-1 for Expression in *E. coli*

An *E. coli* strain expressing GDC-1 was engineered into a customized expression vector (pAX481). pAX481 contains the pBR322 origin of replication, a chloramphenicol acetyl transferase gene (for selection and maintenance of the plasmid), the lacI gene, the Ptac promoter and the rrnB transcriptional terminator. The GDC-1 open reading frame was amplified by PCR using a high fidelity DNA polymerase, as known in the art. The oligonucleotides for PCR amplification of GDC-1 were designed to place the ATG start site of the gene at the proper distance from the ribosome binding site of pAX481.

The GDC-1 PCR product was cloned into the expression vector pAX481 and transformed into *E. coli* XL1 Blue MRF' to yield the plasmid pAX472. GDC-1 positive clones were identified by standard methods known in the art. The sequence of pAX472 was confirmed by DNA sequence analysis as known in the art.

Example 10

Purification of GDC-1 Expressed as a 6×His-tagged Protein in *E. coli*

The GDC-1 coding region (1,728 nucleotides) was amplified by PCR using ProofStart™ DNA polymerase. Oligonucleotides used to prime PCR were designed to introduce restriction enzyme recognition sites near the 5' and 3' ends of the resulting PCR product. The resulting PCR product was digested with BamH I and Sal I. BamH I cleaved the PCR product at the 5' end, and Sal I cleaved the PCR product at the 3' end. The digested product was cloned into the 6×His-tag expression vector pQE-30 (Qiagen), prepared by digestion with BamH I and Sal I. The resulting clone, pAX623, contained GDC-1 in the same translational reading frame as, and immediately C-terminal to, the 6×His tag of pQE-30. General strategies for generating such clones, and for expressing proteins containing 6×His-tag are well known in the art.

The ability of this clone to confer glyphosate resistance was confirmed by plating cells of pAX623 onto M63 media containing 5 mM glyphosate. pAX623-containing cells gave rise to colonies, where cells containing the vector alone gave no colonies.

GDC-1 protein from pAX623-containing cells was isolated by expression of GDC-1-6×His-tagged protein in *E. coli*, and the resulting protein purified using Ni-NTA Superflow Resin (Qiagen) as per manufacturer's instructions.

Example 11

Assay of GDC-1 Pyruvate Decarboxylase Activity 100 ng of GDC-1 protein was tested for activity in a standard pyruvate decarboxylase assay (Gounaris et al. (1971) *J. of Biol. Chem.* 246:1302-1309). This assay is a coupled reaction, wherein the first step the pyruvate decarboxylase (PDC) converts pyruvate to acetaldehyde and $CO_2$. The acetaldehyde produced in this reaction is a substrate for alcohol dehydrogenase, which converts acetaldehyde and β-NADH to ethanol and β-NAD. Thus, PDC activity is detected by virtue of utilization of β-NADH as decrease in absorbance at 340 nM in a spectrophotometer. GDC-1 as well as a control enzyme (pyruvate decarboxylase, Sigma) were tested in this assay. GDC-1 showed activity as a pyruvate decarboxylase, and the reaction rate correlated with the concentration of pyruvate in the assay.

Example 12

Engineering GDC-1 for Plant Transformation

The GDC-1 open reading frame (ORF) was amplified by PCR from a full-length cDNA template. HindIII restriction sites were added to each end of the ORF during PCR. Additionally, the nucleotide sequence ACC was added immediately 5' to the start codon of the gene to increase translational efficiency (Kozak (1987) *Nucleic Acids Research,* 15:8125-8148; Joshi (1987) *Nucleic Acids Research* 15:6643-6653). The PCR product was cloned and sequenced, using techniques well known in the art, to ensure that no mutations were introduced during PCR.

The plasmid containing the GDC-1 PCR product was partially digested with Hind III and the 1.7 kb Hind III fragment containing the intact ORF was isolated. (GDC-1 contains an internal Hind III site in addition to the sites added by PCR.) This fragment was cloned into the Hind III site of plasmid pAX200, a plant expression vector containing the rice actin promoter (McElroy et al. (1991) *Mol. Gen. Genet.* 231:150-160) and the PinII terminator (An et al. (1989) *The Plant Cell* 1:115-122). The promoter—gene—terminator fragment from this intermediate plasmid was subcloned into Xho I site of plasmid pSB11 (Japan Tobacco, Inc.) to form the plasmid pAX810. pAX810 is organized such that the 3.45 kb DNA fragment containing the promoter—GDC-1—terminator construct may be excised from pAX810 by double digestion with KpnI and XbaI for transformation into plants using aerosol beam injection. The structure of pAX810 was verified by restriction digests and gel electrophoresis and by sequencing across the various cloning junctions.

Plasmid pAX810 was mobilized into *Agrobacterium tumifaciens* strain LBA4404 which also harbored the plasmid pSB1 (Japan Tobacco, Inc.), using triparental mating procedures well known in the art, and plated on media containing spectinomycin. Plasmid pAX810 carries spectinomycin resistance but is a narrow host range plasmid and cannot replicate in *Agrobacterium*. Spectinomycin resistant colonies arise when pAX810 integrates into the broad host range plasmid pSB1 through homologous recombination. The cointegrate product of pSB1 and pAX810 was named pAX204 and was verified by Southern hybridization (data not shown). The *Agrobacterium* strain harboring pAX204 was used to transform maize by the PureIntro method (Japan Tobacco).

Example 13

Transformation of GDC-1 into Plant Cells

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D). However, media and salts other than DN62A5S are suitable and are known in the art. Embryos are incubated overnight at 25° C. in the dark.

The resulting explants are transferred to mesh squares (30-40 per plate), transferred onto osmotic media for 30-45 minutes, and then transferred to a beaming plate (see, for example, PCT Publication No. WO/0138514 and U.S. Pat. No. 5,240,842).

DNA constructs designed to express GDC-1 in plant cells are accelerated into plant tissue using an aerosol beam accelerator, using conditions essentially as described in PCT Publication No. WO/0138514. After beaming, embryos are incubated for 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| Components | DN62A5S Media per liter | Source |
|---|---|---|
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3 g/L, and autoclave. After cooling to 50° C., add 2 ml/L of a 5 mg/ml stock solution of Silver Nitrate (Phytotechnology Labs). Recipe yields about 20 plates.

Example 14

Transformation of GDC-1 into Plant Cells by *Agrobacterium*-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule selected from the group consisting of:
   a) a nucleic acid molecule comprising the nucleotide sequence of SEQ ID NO:7;
   b) a nucleic acid molecule which encodes a polypeptide comprising the amino acid sequence of SEQ ID NO:8; and,
   c) complement of a) or b).

2. The isolated nucleic acid molecule of claim 1, wherein said nucleotide sequence is a synthetic sequence that has been designed for expression in a plant.

3. The nucleic acid molecule of claim 2, wherein said synthetic sequence has an increased GC content relative to the GC content of SEQ ID NO:7.

4. A vector comprising the nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A method for conferring resistance to glyphosate in a plant, said method comprising transforming said plant with a DNA construct, said construct comprising a promoter that drives expression in a plant cell operably linked with the nucleotide sequence of SEQ ID NO:7, and regenerating a transformed plant.

13. A plant having stably incorporated into its genome a DNA construct comprising a nucleotide sequence that encodes a protein having glyphosate resistance activity, wherein said nucleotide sequence is selected from the group consisting of:
   a) the nucleotide sequence of SEQ ID NO:7; and,
   b) a nucleotide sequence encoding a polypeptide comprising the amino acid sequence of SEQ ID NO:8;
   wherein said nucleotide sequence is operably linked to a promoter that drives expression of a coding sequence in a plant cell.

14. A plant cell having stably incorporated into its genome a DNA construct comprising a nucleotide sequence that encodes a protein having herbicide resistance activity, wherein said nucleotide sequence is selected from the group consisting of:
   a) the nucleotide sequence of SEQ ID NO:7; and,
   b) a nucleotide sequence encoding a polypeptide comprising the amino acid sequence of SEQ ID NO:8;
   wherein said nucleotide sequence is operably linked to a promoter that drives expression of a coding sequence in a plant cell.

* * * * *

SEQUENCE LISTING

```
<160> NUMBER OF SEQ ID NOS: 21

<210> SEQ ID NO 1
<211> LENGTH: 2210
<212> TYPE: DNA
<213> ORGANISM: Unknown
<220> FEATURE:
<221> NAME/KEY: CDS
<222> LOCATION: (224)...(1951)
<223> OTHER INFORMATION: Fungal isolate from soil sample

<400> SEQUENCE: 1
acgcggggtg cccacggaca acaattccct taggattatc tcctgtattg aatacactct        60
actttgcaac tttacctatt attcgacttt cttttagagg agcagcattg tcatcattac       120
ctgcccctcc atctgatacc taccttacat tgtcgccaac acacctataa gccataatat       180
accgactcaa agcaaaccac gcccattgtt tgattgttta atc atg gcc agc atc        235
                                                Met Ala Ser Ile
                                                  1 aac atc agg gtg cag aat ctc gag caa ccc atg gac gtt gcc gag tat        283
Asn Ile Arg Val Gln Asn Leu Glu Gln Pro Met Asp Val Ala Glu Tyr
  5                  10                  15                  20 ctt ttt cgg cgt ctc cac gaa atc ggc att cgc tcc atc cac ggt ctt        331
Leu Phe Arg Arg Leu His Glu Ile Gly Ile Arg Ser Ile His Gly Leu
                 25                  30                  35 cca ggc gat tac aac ctt ctt gcc ctc gac tat ttg cca tca tgt ggc        379
Pro Gly Asp Tyr Asn Leu Leu Ala Leu Asp Tyr Leu Pro Ser Cys Gly
             40                  45                  50 ctg aga tgg gtt ggc agc gtc aac gaa ctc aat gct gct tat gct gct        427
Leu Arg Trp Val Gly Ser Val Asn Glu Leu Asn Ala Ala Tyr Ala Ala
         55                  60                  65 gat ggc tat gcc cgc gtc aag cag atg gga gct ctc atc acc act ttt        475
Asp Gly Tyr Ala Arg Val Lys Gln Met Gly Ala Leu Ile Thr Thr Phe
     70                  75                  80 gga gtg gga gag ctc tca gcc atc aat ggc gtt gcc ggt gcc ttt tcg        523
Gly Val Gly Glu Leu Ser Ala Ile Asn Gly Val Ala Gly Ala Phe Ser
 85                  90                  95                 100 gaa cac gtc cca gtc gtt cac att gtt ggc tgc cct tcc act gtc tcg        571
Glu His Val Pro Val Val His Ile Val Gly Cys Pro Ser Thr Val Ser
                105                 110                 115 cag cga aac ggc atg ctc ctc cac cac acg ctt gga aac ggc gac ttc        619
Gln Arg Asn Gly Met Leu Leu His His Thr Leu Gly Asn Gly Asp Phe
            120                 125                 130 aac atc ttt gcc aac atg agc gct caa atc tct tgc gaa gtg gcc aag        667
Asn Ile Phe Ala Asn Met Ser Ala Gln Ile Ser Cys Glu Val Ala Lys
        135                 140                 145 ctc acc aac cct gcc gaa att gcg acc cag atc gac cat gcc ctc cgc        715
Leu Thr Asn Pro Ala Glu Ile Ala Thr Gln Ile Asp His Ala Leu Arg
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 150 |     |     |     |     | 155 |     |     |     |     | 160 |     |     |      |
| gtt | tgc | ttc | att | cgt | tct | cgg | ccc | gtc | tac | atc | atg | ctt | ccc | acc | gat | 763  |
| Val | Cys | Phe | Ile | Arg | Ser | Arg | Pro | Val | Tyr | Ile | Met | Leu | Pro | Thr | Asp |      |
| 165 |     |     |     |     | 170 |     |     |     |     | 175 |     |     |     |     | 180 |      |
| atg | gtc | cag | gcc | aaa | gta | gaa | ggt | gcc | aga | ctc | aag | gaa | cca | att | gac | 811  |
| Met | Val | Gln | Ala | Lys | Val | Glu | Gly | Ala | Arg | Leu | Lys | Glu | Pro | Ile | Asp |      |
|     |     |     |     | 185 |     |     |     |     | 190 |     |     |     |     | 195 |     |      |
| ttg | tcg | gag | cct | cca | aat | gat | ccc | gag | aaa | gaa | gca | tac | gtc | gtt | gac | 859  |
| Leu | Ser | Glu | Pro | Pro | Asn | Asp | Pro | Glu | Lys | Glu | Ala | Tyr | Val | Val | Asp |      |
|     |     |     | 200 |     |     |     |     | 205 |     |     |     |     | 210 |     |     |      |
| gtt | gtc | ctc | aag | tay | ctc | cgt | gct | gca | aag | aac | ccc | gtc | atc | ctt | gtc | 907  |
| Val | Val | Leu | Lys | Tyr | Leu | Arg | Ala | Ala | Lys | Asn | Pro | Val | Ile | Leu | Val |      |
|     |     |     | 215 |     |     |     |     | 220 |     |     |     |     | 225 |     |     |      |
| gat | gct | tgt | gct | atc | cgt | cat | cgt | gtt | ctt | gat | gag | gtt | cat | gat | ctc | 955  |
| Asp | Ala | Cys | Ala | Ile | Arg | His | Arg | Val | Leu | Asp | Glu | Val | His | Asp | Leu |      |
|     |     | 230 |     |     |     |     | 235 |     |     |     |     | 240 |     |     |     |      |
| atc | gaa | aag | aca | aac | ctc | cct | gtc | ttt | gtc | act | cct | atg | ggc | aaa | ggt | 1003 |
| Ile | Glu | Lys | Thr | Asn | Leu | Pro | Val | Phe | Val | Thr | Pro | Met | Gly | Lys | Gly |      |
| 245 |     |     |     |     | 250 |     |     |     |     | 255 |     |     |     |     | 260 |      |
| gct | gtt | aac | gaa | gaa | cac | ccg | aca | tat | ggt | ggt | gtc | tat | gcc | ggt | gac | 1051 |
| Ala | Val | Asn | Glu | Glu | His | Pro | Thr | Tyr | Gly | Gly | Val | Tyr | Ala | Gly | Asp |      |
|     |     |     |     | 265 |     |     |     |     | 270 |     |     |     |     | 275 |     |      |
| ggc | tca | cat | ccg | cct | caa | gtt | aag | gac | atg | gtt | gag | tct | tct | gat | ttg | 1099 |
| Gly | Ser | His | Pro | Pro | Gln | Val | Lys | Asp | Met | Val | Glu | Ser | Ser | Asp | Leu |      |
|     |     |     | 280 |     |     |     |     | 285 |     |     |     |     | 290 |     |     |      |
| ata | ttg | aca | atc | ggt | gct | ctc | aag | agc | gac | ttc | aac | act | gct | ggc | ttc | 1147 |
| Ile | Leu | Thr | Ile | Gly | Ala | Leu | Lys | Ser | Asp | Phe | Asn | Thr | Ala | Gly | Phe |      |
|     |     | 295 |     |     |     |     | 300 |     |     |     |     | 305 |     |     |     |      |
| tct | tac | cgt | acc | tca | cag | ctg | aac | acg | att | gat | cta | cac | agc | gac | cac | 1195 |
| Ser | Tyr | Arg | Thr | Ser | Gln | Leu | Asn | Thr | Ile | Asp | Leu | His | Ser | Asp | His |      |
|     |     | 310 |     |     |     |     | 315 |     |     |     |     | 320 |     |     |     |      |
| tgc | att | gtc | aaa | tac | tcg | aca | tat | cca | ggt | gtc | cag | atg | agg | ggt | gtg | 1243 |
| Cys | Ile | Val | Lys | Tyr | Ser | Thr | Tyr | Pro | Gly | Val | Gln | Met | Arg | Gly | Val |      |
| 325 |     |     |     |     | 330 |     |     |     |     | 335 |     |     |     |     | 340 |      |
| ctg | cga | caa | gtg | att | aag | cag | ctc | gat | gca | tct | gag | atc | aac | gct | cag | 1291 |
| Leu | Arg | Gln | Val | Ile | Lys | Gln | Leu | Asp | Ala | Ser | Glu | Ile | Asn | Ala | Gln |      |
|     |     |     |     | 345 |     |     |     |     | 350 |     |     |     |     | 355 |     |      |
| cca | gcg | cca | gtc | gtc | gag | aat | gaa | gtt | gcc | aaa | aac | cga | gat | aac | tca | 1339 |
| Pro | Ala | Pro | Val | Val | Glu | Asn | Glu | Val | Ala | Lys | Asn | Arg | Asp | Asn | Ser |      |
|     |     |     | 360 |     |     |     |     | 365 |     |     |     |     | 370 |     |     |      |
| ccc | gtc | att | aca | caa | gct | ttc | ttc | tgg | ccg | cgc | gtg | gga | gag | ttc | ctg | 1387 |
| Pro | Val | Ile | Thr | Gln | Ala | Phe | Phe | Trp | Pro | Arg | Val | Gly | Glu | Phe | Leu |      |
|     |     | 375 |     |     |     |     | 380 |     |     |     |     | 385 |     |     |     |      |
| aag | aag | aac | gac | atc | gtc | att | acc | gag | act | gga | aca | gcc | aac | ttt | ggc | 1435 |
| Lys | Lys | Asn | Asp | Ile | Val | Ile | Thr | Glu | Thr | Gly | Thr | Ala | Asn | Phe | Gly |      |
|     | 390 |     |     |     |     | 395 |     |     |     |     | 400 |     |     |     |     |      |
| atc | tgg | gat | act | aag | ttt | ccc | tct | ggc | gtt | act | gcg | ctt | tct | cag | gtc | 1483 |
| Ile | Trp | Asp | Thr | Lys | Phe | Pro | Ser | Gly | Val | Thr | Ala | Leu | Ser | Gln | Val |      |
| 405 |     |     |     |     | 410 |     |     |     |     | 415 |     |     |     |     | 420 |      |
| ctt | tgg | gga | agc | att | ggt | tgg | tcc | gtt | ggt | gcc | tgc | caa | gga | gcc | gtt | 1531 |
| Leu | Trp | Gly | Ser | Ile | Gly | Trp | Ser | Val | Gly | Ala | Cys | Gln | Gly | Ala | Val |      |
|     |     |     |     | 425 |     |     |     |     | 430 |     |     |     |     | 435 |     |      |
| ctt | gca | gcc | gcc | gat | gac | aac | agc | gat | cgc | aga | act | atc | ctc | ttt | gtt | 1579 |
| Leu | Ala | Ala | Ala | Asp | Asp | Asn | Ser | Asp | Arg | Arg | Thr | Ile | Leu | Phe | Val |      |
|     |     |     | 440 |     |     |     |     | 445 |     |     |     |     | 450 |     |     |      |
| ggt | gat | ggc | tca | ttc | cag | ctc | act | gct | caa | gaa | ttg | agc | aca | atg | att | 1627 |
| Gly | Asp | Gly | Ser | Phe | Gln | Leu | Thr | Ala | Gln | Glu | Leu | Ser | Thr | Met | Ile |      |
|     |     |     | 455 |     |     |     |     | 460 |     |     |     |     | 465 |     |     |      |
| cgt | ctc | aag | ctg | aag | ccc | atc | atc | ttt | gtc | atc | tgc | aac | gat | ggc | ttt | 1675 |

```
Arg Leu Lys Leu Lys Pro Ile Ile Phe Val Ile Cys Asn Asp Gly Phe
    470                 475                 480 acc att gaa cga ttc att cac ggc atg gaa gcc gag tac aac gac atc    1723
Thr Ile Glu Arg Phe Ile His Gly Met Glu Ala Glu Tyr Asn Asp Ile
485                 490                 495                 500 gca aat tgg gac ttc aag gct ctg gtt gac gtc ttt ggc ggc tct aag    1771
Ala Asn Trp Asp Phe Lys Ala Leu Val Asp Val Phe Gly Gly Ser Lys
                505                 510                 515 acg gcc aag aag ttc gcc gtc aag acc aag gac gag ctg gac agc ctt    1819
Thr Ala Lys Lys Phe Ala Val Lys Thr Lys Asp Glu Leu Asp Ser Leu
            520                 525                 530 ctc aca gac cct acc ttt aac gcc gca gaa tgc ctc cag ttt gtc gag    1867
Leu Thr Asp Pro Thr Phe Asn Ala Ala Glu Cys Leu Gln Phe Val Glu
        535                 540                 545 cta tat atg ccc aaa gaa gat gct cct cga gca ttg atc atg act gca    1915
Leu Tyr Met Pro Lys Glu Asp Ala Pro Arg Ala Leu Ile Met Thr Ala
    550                 555                 560 gaa gct agc gcg agg aac aat gcc aag aca gag taa agtggactgt         1961
Glu Ala Ser Ala Arg Asn Asn Ala Lys Thr Glu  *
565                 570                 575 catgaaggcc gatttaccac ctcataaatt gtaatagacc tgatacacat agatcaaggc   2021
aggtaccgat cattaatcaa gcaggtttgg atggggaagg attttgaaaa tgaggaaacg   2081
atgggatgat atttggaata actggccatt attttgagta cttataaaca aatttgaagt   2141 tcaattttttt ttcaaaaaaa aaaaaaaaaa aaaaaaaaaa aaaaaaaaaa aaaaaaaaaa   2201
aaaaaaaaa                                                          2210

<210> SEQ ID NO 2
<211> LENGTH: 1725
<212> TYPE: DNA
<213> ORGANISM: Unknown
<220> FEATURE:
<221> NAME/KEY: CDS
<222> LOCATION: (1)...(1725)
<223> OTHER INFORMATION: Fungal isolate from soil sample

<400> SEQUENCE: 2 atg gcc agc atc aac atc agg gtg cag aat ctc gag caa ccc atg gac    48
Met Ala Ser Ile Asn Ile Arg Val Gln Asn Leu Glu Gln Pro Met Asp
1               5                   10                  15 gtt gcc gag tat ctt ttt cgg cgt ctc cac gaa atc ggc att cgc tcc    96
Val Ala Glu Tyr Leu Phe Arg Arg Leu His Glu Ile Gly Ile Arg Ser
            20                  25                  30 atc cac ggt ctt cca ggc gat tac aac ctt ctt gcc ctc gac tat ttg    144
Ile His Gly Leu Pro Gly Asp Tyr Asn Leu Leu Ala Leu Asp Tyr Leu
        35                  40                  45 cca tca tgt ggc ctg aga tgg gtt ggc agc gtc aac gaa ctc aat gct    192
Pro Ser Cys Gly Leu Arg Trp Val Gly Ser Val Asn Glu Leu Asn Ala
    50                  55                  60 gct tat gct gct gat ggc tat gcc cgc gtc aag cag atg gga gct ctc    240
Ala Tyr Ala Ala Asp Gly Tyr Ala Arg Val Lys Gln Met Gly Ala Leu
65                  70                  75                  80 atc acc act ttt gga gtg gga gag ctc tca gcc atc aat ggc gtt gcc    288
Ile Thr Thr Phe Gly Val Gly Glu Leu Ser Ala Ile Asn Gly Val Ala
                85                  90                  95 ggt gcc ttt tcg gaa cac gtc cca gtc gtt cac att gtt ggc tgc cct    336
Gly Ala Phe Ser Glu His Val Pro Val Val His Ile Val Gly Cys Pro
            100                 105                 110 tcc act gtc tcg cag cga aac ggc atg ctc ctc cac cac acg ctt gga    384
Ser Thr Val Ser Gln Arg Asn Gly Met Leu Leu His His Thr Leu Gly
```

```
                115                 120                 125
aac ggc gac ttc aac atc ttt gcc aac atg agc gct caa atc tct tgc    432
Asn Gly Asp Phe Asn Ile Phe Ala Asn Met Ser Ala Gln Ile Ser Cys
    130                 135                 140 gaa gtg gcc aag ctc acc aac cct gcc gaa att gcg acc cag atc gac    480
Glu Val Ala Lys Leu Thr Asn Pro Ala Glu Ile Ala Thr Gln Ile Asp
145                 150                 155                 160 cat gcc ctc cgc gtt tgc ttc att cgt tct cgg ccc gtc tac atc atg    528
His Ala Leu Arg Val Cys Phe Ile Arg Ser Arg Pro Val Tyr Ile Met
                165                 170                 175 ctt ccc acc gat atg gtc cag gcc aaa gta gaa ggt gcc aga ctc aag    576
Leu Pro Thr Asp Met Val Gln Ala Lys Val Glu Gly Ala Arg Leu Lys
            180                 185                 190 gaa cca att gac ttg tcg gag cct cca aat gat ccc gag aaa gaa gca    624
Glu Pro Ile Asp Leu Ser Glu Pro Pro Asn Asp Pro Glu Lys Glu Ala
        195                 200                 205 tac gtc gtt gac gtt gtc ctc aag tay ctc cgt gct gca aag aac ccc    672
Tyr Val Val Asp Val Val Leu Lys Tyr Leu Arg Ala Ala Lys Asn Pro
    210                 215                 220 gtc atc ctt gtc gat gct tgt gct atc cgt cat cgt gtt ctt gat gag    720
Val Ile Leu Val Asp Ala Cys Ala Ile Arg His Arg Val Leu Asp Glu
225                 230                 235                 240 gtt cat gat ctc atc gaa aag aca aac ctc cct gtc ttt gtc act cct    768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc    816
Met Gly Lys Gly Ala Val Asn Glu Glu His Pro Thr Tyr Gly Gly Val
            260                 265                 270 tat gcc ggt gac ggc tca cat ccg cct caa gtt aag gac atg gtt gag    864
Tyr Ala Gly Asp Gly Ser His Pro Pro Gln Val Lys Asp Met Val Glu
        275                 280                 285 tct tct gat ttg ata ttg aca atc ggt gct ctc aag agc gac ttc aac    912
Ser Ser Asp Leu Ile Leu Thr Ile Gly Ala Leu Lys Ser Asp Phe Asn
    290                 295                 300 act gct ggc ttc tct tac cgt acc tca cag ctg aac acg att gat cta    960
Thr Ala Gly Phe Ser Tyr Arg Thr Ser Gln Leu Asn Thr Ile Asp Leu
305                 310                 315                 320 cac agc gac cac tgc att gtc aaa tac tcg aca tat cca ggt gtc cag   1008
His Ser Asp His Cys Ile Val Lys Tyr Ser Thr Tyr Pro Gly Val Gln
                325                 330                 335 atg agg ggt gtg ctg cga caa gtg att aag cag ctc gat gca tct gag   1056
Met Arg Gly Val Leu Arg Gln Val Ile Lys Gln Leu Asp Ala Ser Glu
            340                 345                 350 atc aac gct cag cca gcg cca gtc gtc gag aat gaa gtt gcc aaa aac   1104
Ile Asn Ala Gln Pro Ala Pro Val Val Glu Asn Glu Val Ala Lys Asn
        355                 360                 365 cga gat aac tca ccc gtc att aca caa gct ttc ttc tgg ccg cgc gtg   1152
Arg Asp Asn Ser Pro Val Ile Thr Gln Ala Phe Phe Trp Pro Arg Val
    370                 375                 380 gga gag ttc ctg aag aag aac gac atc gtc att acc gag act gga aca   1200
Gly Glu Phe Leu Lys Lys Asn Asp Ile Val Ile Thr Glu Thr Gly Thr
385                 390                 395                 400 gcc aac ttt ggc atc tgg gat act aag ttt ccc tct ggc gtt act gcg   1248
Ala Asn Phe Gly Ile Trp Asp Thr Lys Phe Pro Ser Gly Val Thr Ala
                405                 410                 415 ctt tct cag gtc ctt tgg gga agc att ggt tgg tcc gtt ggt gcc tgc   1296
Leu Ser Gln Val Leu Trp Gly Ser Ile Gly Trp Ser Val Gly Ala Cys
            420                 425                 430 caa gga gcc gtt ctt gca gcc gcc gat gac aac agc gat cgc aga act   1344
```

```
Gln Gly Ala Val Leu Ala Ala Ala Asp Asp Asn Ser Asp Arg Arg Thr
            435                 440                 445 atc ctc ttt gtt ggt gat ggc tca ttc cag ctc act gct caa gaa ttg    1392
Ile Leu Phe Val Gly Asp Gly Ser Phe Gln Leu Thr Ala Gln Glu Leu
        450                 455                 460 agc aca atg att cgt ctc aag ctg aag ccc atc atc ttt gtc atc tgc    1440
Ser Thr Met Ile Arg Leu Lys Leu Lys Pro Ile Ile Phe Val Ile Cys
465                 470                 475                 480 aac gat ggc ttt acc att gaa cga ttc att cac ggc atg gaa gcc gag    1488
Asn Asp Gly Phe Thr Ile Glu Arg Phe Ile His Gly Met Glu Ala Glu
                485                 490                 495 tac aac gac atc gca aat tgg gac ttc aag gct ctg gtt gac gtc ttt    1536
Tyr Asn Asp Ile Ala Asn Trp Asp Phe Lys Ala Leu Val Asp Val Phe
            500                 505                 510 ggc ggc tct aag acg gcc aag aag ttc gcc gtc aag acc aag gac gag    1584
Gly Gly Ser Lys Thr Ala Lys Lys Phe Ala Val Lys Thr Lys Asp Glu
        515                 520                 525 ctg gac agc ctt ctc aca gac cct acc ttt aac gcc gca gaa tgc ctc    1632
Leu Asp Ser Leu Leu Thr Asp Pro Thr Phe Asn Ala Ala Glu Cys Leu
    530                 535                 540 cag ttt gtc gag cta tat atg ccc aaa gaa gat gct cct cga gca ttg    1680
Gln Phe Val Glu Leu Tyr Met Pro Lys Glu Asp Ala Pro Arg Ala Leu
545                 550                 555                 560 atc atg act gca gaa gct agc gcg agg aac aat gcc aag aca gag         1725
Ile Met Thr Ala Glu Ala Ser Ala Arg Asn Asn Ala Lys Thr Glu
                565                 570                 575

<210> SEQ ID NO 3
<211> LENGTH: 575
<212> TYPE: PRT
<213> ORGANISM: Unknown
<220> FEATURE:
<223> OTHER INFORMATION: Fungal isolate from soil sample

<400> SEQUENCE: 3

Met Ala Ser Ile Asn Ile Arg Val Gln Asn Leu Glu Gln Pro Met Asp
  1               5                  10                  15

Val Ala Glu Tyr Leu Phe Arg Arg Leu His Ile Gly Ile Arg Ser
                 20                  25                  30

Ile His Gly Leu Pro Gly Asp Tyr Asn Leu Leu Ala Leu Asp Tyr Leu
             35                  40                  45

Pro Ser Cys Gly Leu Arg Trp Val Gly Ser Val Asn Glu Leu Asn Ala
         50                  55                  60

Ala Tyr Ala Ala Asp Gly Tyr Ala Arg Val Lys Gln Met Gly Ala Leu
 65                  70                  75                  80

Ile Thr Thr Phe Gly Val Gly Glu Leu Ser Ala Ile Asn Gly Val Ala
                 85                  90                  95

Gly Ala Phe Ser Glu His Val Pro Val Val His Ile Val Gly Cys Pro
            100                 105                 110

Ser Thr Val Ser Gln Arg Asn Gly Met Leu Leu His His Thr Leu Gly
        115                 120                 125

Asn Gly Asp Phe Asn Ile Phe Ala Asn Met Ser Ala Gln Ile Ser Cys
    130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
                165                 170                 175

Leu Pro Thr Asp Met Val Gln Ala Lys Val Glu Gly Ala Arg Leu Lys
```

|     |     |     |     |     |     |     |     |     |     |     |     |
| --- | --- | --- | --- | --- | --- | --- | --- | --- | --- | --- | --- |
|     |     |     | 180 |     |     | 185 |     |     | 190 |     |     |
| Glu | Pro | Ile | Asp | Leu | Ser | Glu | Pro | Asn | Asp | Pro | Glu | Lys | Glu | Ala |

(Positions 193–575 continue in groups of 15 residues per row)

```
                180                 185                 190
Glu Pro Ile Asp Leu Ser Glu Pro Asn Asp Pro Glu Lys Glu Ala
            195                 200                 205
Tyr Val Asp Val Val Leu Lys Tyr Leu Arg Ala Ala Lys Asn Pro
        210                 215                 220
Val Ile Leu Val Asp Ala Cys Ala Ile Arg His Arg Val Leu Asp Glu
225                 230                 235                 240
Val His Asp Leu Ile Glu Lys Thr Asn Leu Pro Val Phe Val Thr Pro
                245                 250                 255
Met Gly Lys Gly Ala Val Asn Glu Glu His Pro Thr Tyr Gly Gly Val
            260                 265                 270
Tyr Ala Gly Asp Gly Ser His Pro Pro Gln Val Lys Asp Met Val Glu
        275                 280                 285
Ser Ser Asp Leu Ile Leu Thr Ile Gly Ala Leu Lys Ser Asp Phe Asn
    290                 295                 300
Thr Ala Gly Phe Ser Tyr Arg Thr Ser Gln Leu Asn Thr Ile Asp Leu
305                 310                 315                 320
His Ser Asp His Cys Ile Val Lys Tyr Ser Thr Tyr Pro Gly Val Gln
                325                 330                 335
Met Arg Gly Val Leu Arg Gln Val Ile Lys Gln Leu Asp Ala Ser Glu
            340                 345                 350
Ile Asn Ala Gln Pro Ala Pro Val Val Glu Asn Glu Val Ala Lys Asn
        355                 360                 365
Arg Asp Asn Ser Pro Val Ile Thr Gln Ala Phe Phe Trp Pro Arg Val
    370                 375                 380
Gly Glu Phe Leu Lys Lys Asn Asp Ile Val Ile Thr Glu Thr Gly Thr
385                 390                 395                 400
Ala Asn Phe Gly Ile Trp Asp Thr Lys Phe Pro Ser Gly Val Thr Ala
                405                 410                 415
Leu Ser Gln Val Leu Trp Gly Ser Ile Gly Trp Ser Val Gly Ala Cys
            420                 425                 430
Gln Gly Ala Val Leu Ala Ala Asp Asp Asn Ser Asp Arg Arg Thr
        435                 440                 445
Ile Leu Phe Val Gly Asp Gly Ser Phe Gln Leu Thr Ala Gln Glu Leu
    450                 455                 460
Ser Thr Met Ile Arg Leu Lys Leu Lys Pro Ile Ile Phe Val Ile Cys
465                 470                 475                 480
Asn Asp Gly Phe Thr Ile Glu Arg Phe Ile His Gly Met Glu Ala Glu
                485                 490                 495
Tyr Asn Asp Ile Ala Asn Trp Asp Phe Lys Ala Leu Val Asp Val Phe
            500                 505                 510
Gly Gly Ser Lys Thr Ala Lys Lys Phe Ala Val Lys Thr Lys Asp Glu
        515                 520                 525
Leu Asp Ser Leu Leu Thr Asp Pro Thr Phe Asn Ala Ala Glu Cys Leu
    530                 535                 540
Gln Phe Val Glu Leu Tyr Met Pro Lys Glu Asp Ala Pro Arg Ala Leu
545                 550                 555                 560
Ile Met Thr Ala Glu Ala Ser Ala Arg Asn Asn Ala Lys Thr Glu
                565                 570                 575
```

<210> SEQ ID NO 4
<211> LENGTH: 835
<212> TYPE: DNA
<213> ORGANISM: Unknown

-continued

```
<220> FEATURE:
<221> NAME/KEY: CDS
<222> LOCATION: (3)...(596)
<223> OTHER INFORMATION: Fungal isolate from soil sample

<400> SEQUENCE: 4 ct ttc ttc tgg ccg cgc gtg gga gag ttc ctg aag aag aac gac atc         47
   Phe Phe Trp Pro Arg Val Gly Glu Phe Leu Lys Lys Asn Asp Ile
    1               5                   10                  15 gtc att acc gag act gga aca gcc aac ttt ggc atc tgg gat act aag        95
Val Ile Thr Glu Thr Gly Thr Ala Asn Phe Gly Ile Trp Asp Thr Lys
             20                  25                  30 ttt ccc tct ggc gtt act gcg ctt tct cag gtc ctt tgg gga agc att       143
Phe Pro Ser Gly Val Thr Ala Leu Ser Gln Val Leu Trp Gly Ser Ile
         35                  40                  45 ggt tgg tcc gtt ggt gcc tgc caa gga gcc gtt ctt gca gcc gcc gat       191
Gly Trp Ser Val Gly Ala Cys Gln Gly Ala Val Leu Ala Ala Ala Asp
     50                  55                  60 gac aac agc gat cgc aga act atc ctc ttt gtt ggt gat ggc tca ttc       239
Asp Asn Ser Asp Arg Arg Thr Ile Leu Phe Val Gly Asp Gly Ser Phe
 65                  70                  75 cag ctc act gct caa gaa ttg agc aca atg att cgt ctc aag ctg aag       287
Gln Leu Thr Ala Gln Glu Leu Ser Thr Met Ile Arg Leu Lys Leu Lys
 80                  85                  90                  95 ccc atc atc ttt gtc atc tgc aac gat ggc ttt acc att gaa cga ttc       335
Pro Ile Ile Phe Val Ile Cys Asn Asp Gly Phe Thr Ile Glu Arg Phe
                100                 105                 110 att cac ggc atg gaa gcc gag tac aac gac atc gca aat tgg gac ttc       383
Ile His Gly Met Glu Ala Glu Tyr Asn Asp Ile Ala Asn Trp Asp Phe
            115                 120                 125 aag gct ctg gtt gac gtc ttt ggc ggc tct aag acg gcc aag aag ttc       431
Lys Ala Leu Val Asp Val Phe Gly Gly Ser Lys Thr Ala Lys Lys Phe
        130                 135                 140 gcc gtc aag acc aag gac gag ctg gac agc ctt ctc aca gac cct acc       479
Ala Val Lys Thr Lys Asp Glu Leu Asp Ser Leu Leu Thr Asp Pro Thr
    145                 150                 155 ttt aac gcc gca gaa tgc ctc cag ttt gtc gag cta tat atg ccc aaa       527
Phe Asn Ala Ala Glu Cys Leu Gln Phe Val Glu Leu Tyr Met Pro Lys
160                 165                 170                 175 gaa gat gct cct cga gca ttg atc atg act gca gaa gct agc gcg agg       575
Glu Asp Ala Pro Arg Ala Leu Ile Met Thr Ala Glu Ala Ser Ala Arg
                180                 185                 190 aac aat gcc aag aca gag taa agtggactgt catgaaggcc gatttaccac         626
Asn Asn Ala Lys Thr Glu  *
                195 ctcataaatt gtaatagacc tgatacacat agatcaaggc aggtaccgat cattaatcaa    686 gcaggtttgg atggggaagg atttgaaaa tgaggaaacg atgggatgat atttggaata    746 actggccatt attttgagta cttataaaca aatttgaagt tcaatttttt ttcaaaaaaa    806 aaaaaaaaaa aaaaaaaaa aaaaaaaa                                       835

<210> SEQ ID NO 5
<211> LENGTH: 591
<212> TYPE: DNA
<213> ORGANISM: Unknown
<220> FEATURE:
<221> NAME/KEY: CDS
<222> LOCATION: (1)...(591)
<223> OTHER INFORMATION: Fungal isolate from soil sample

<400> SEQUENCE: 5
```

| | | |
|---|---|---|
| ttc ttc tgg ccg cgc gtg gga gag ttc ctg aag aag aac gac atc gtc<br>Phe Phe Trp Pro Arg Val Gly Glu Phe Leu Lys Lys Asn Asp Ile Val<br>1               5                   10                  15 | | 48 |
| att acc gag act gga aca gcc aac ttt ggc atc tgg gat act aag ttt<br>Ile Thr Glu Thr Gly Thr Ala Asn Phe Gly Ile Trp Asp Thr Lys Phe<br>            20                  25                  30 | | 96 |
| ccc tct ggc gtt act gcg ctt tct cag gtc ctt tgg gga agc att ggt<br>Pro Ser Gly Val Thr Ala Leu Ser Gln Val Leu Trp Gly Ser Ile Gly<br>        35                  40                  45 | | 144 |
| tgg tcc gtt ggt gcc tgc caa gga gcc gtt ctt gca gcc gcc gat gac<br>Trp Ser Val Gly Ala Cys Gln Gly Ala Val Leu Ala Ala Ala Asp Asp<br>    50                  55                  60 | | 192 |
| aac agc gat cgc aga act atc ctc ttt gtt ggt gat ggc tca ttc cag<br>Asn Ser Asp Arg Arg Thr Ile Leu Phe Val Gly Asp Gly Ser Phe Gln<br>65                  70                  75                  80 | | 240 |
| ctc act gct caa gaa ttg agc aca atg att cgt ctc aag ctg aag ccc<br>Leu Thr Ala Gln Glu Leu Ser Thr Met Ile Arg Leu Lys Leu Lys Pro<br>                85                  90                  95 | | 288 |
| atc atc ttt gtc atc tgc aac gat ggc ttt acc att gaa cga ttc att<br>Ile Ile Phe Val Ile Cys Asn Asp Gly Phe Thr Ile Glu Arg Phe Ile<br>            100                 105                 110 | | 336 |
| cac ggc atg gaa gcc gag tac aac gac atc gca aat tgg gac ttc aag<br>His Gly Met Glu Ala Glu Tyr Asn Asp Ile Ala Asn Trp Asp Phe Lys<br>        115                 120                 125 | | 384 |
| gct ctg gtt gac gtc ttt ggc ggc tct aag acg gcc aag aag ttc gcc<br>Ala Leu Val Asp Val Phe Gly Gly Ser Lys Thr Ala Lys Lys Phe Ala<br>    130                 135                 140 | | 432 |
| gtc aag acc aag gac gag ctg gac agc ctt ctc aca gac cct acc ttt<br>Val Lys Thr Lys Asp Glu Leu Asp Ser Leu Leu Thr Asp Pro Thr Phe<br>145                 150                 155                 160 | | 480 |
| aac gcc gca gaa tgc ctc cag ttt gtc gag cta tat atg ccc aaa gaa<br>Asn Ala Ala Glu Cys Leu Gln Phe Val Glu Leu Tyr Met Pro Lys Glu<br>                165                 170                 175 | | 528 |
| gat gct cct cga gca ttg atc atg act gca gaa gct agc gcg agg aac<br>Asp Ala Pro Arg Ala Leu Ile Met Thr Ala Glu Ala Ser Ala Arg Asn<br>            180                 185                 190 | | 576 |
| aat gcc aag aca gag<br>Asn Ala Lys Thr Glu<br>        195 | | 591 |

```
<210> SEQ ID NO 6
<211> LENGTH: 197
<212> TYPE: PRT
<213> ORGANISM: Unknown
<220> FEATURE:
<223> OTHER INFORMATION: Fungal isolate from soil sample

<400> SEQUENCE: 6
```

Phe Phe Trp Pro Arg Val Gly Glu Phe Leu Lys Lys Asn Asp Ile Val
1               5                   10                  15

```
Ile Ile Phe Val Ile Cys Asn Asp Gly Phe Thr Ile Glu Arg Phe Ile
            100                 105                 110

His Gly Met Glu Ala Glu Tyr Asn Asp Ile Ala Asn Trp Asp Phe Lys
        115                 120                 125

Ala Leu Val Asp Val Phe Gly Gly Ser Lys Thr Ala Lys Lys Phe Ala
    130                 135                 140

Val Lys Thr Lys Asp Glu Leu Asp Ser Leu Thr Asp Pro Thr Phe
145                 150                 155                 160

Asn Ala Ala Glu Cys Leu Gln Phe Val Glu Leu Tyr Met Pro Lys Glu
                165                 170                 175

Asp Ala Pro Arg Ala Leu Ile Met Thr Ala Glu Ala Ser Ala Arg Asn
            180                 185                 190

Asn Ala Lys Thr Glu
        195

<210> SEQ ID NO 7
<211> LENGTH: 678
<212> TYPE: DNA
<213> ORGANISM: Unknown
<220> FEATURE:
<221> NAME/KEY: CDS
<222> LOCATION: (1)...(678)
<223> OTHER INFORMATION: Fungal isolate from soil sample

<400> SEQUENCE: 7 aca tat cca ggt gtc cag atg agg ggt gtg ctg cga caa gtg att aag     48
Thr Tyr Pro Gly Val Gln Met Arg Gly Val Leu Arg Gln Val Ile Lys
  1               5                  10                  15 cag ctc gat gca tct gag atc aac gct cag cca gcg cca gtc gtc gag     96
Gln Leu Asp Ala Ser Glu Ile Asn Ala Gln Pro Ala Pro Val Val Glu
             20                  25                  30 aat gaa gtt gcc aaa aac cga gat aac tca ccc gtc att aca caa gct    144
Asn Glu Val Ala Lys Asn Arg Asp Asn Ser Pro Val Ile Thr Gln Ala
         35                  40                  45 ttc ttc tgg ccg cgc gtg gga gag ttc ctg aag aag aac gac atc gtc    192
Phe Phe Trp Pro Arg Val Gly Glu Phe Leu Lys Lys Asn Asp Ile Val
     50                  55                  60 att acc gag act gga aca gcc aac ttt ggc atc tgg gat act aag ttt    240
Ile Thr Glu Thr Gly Thr Ala Asn Phe Gly Ile Trp Asp Thr Lys Phe
 65                  70                  75                  80 ccc tct ggc gtt act gcg ctt tct cag gtc ctt tgg gga agc att ggt    288
Pro Ser Gly Val Thr Ala Leu Ser Gln Val Leu Trp Gly Ser Ile Gly
                 85                  90                  95 tgg tcc gtt ggt gcc tgc caa gga gcc gtt ctt gca gcc gcc gat gac    336
Trp Ser Val Gly Ala Cys Gln Gly Ala Val Leu Ala Ala Ala Asp Asp
            100                 105                 110 aac agc gat cgc aga act atc ctc ttt gtt ggt gat ggc tca ttc cag    384
Asn Ser Asp Arg Arg Thr Ile Leu Phe Val Gly Asp Gly Ser Phe Gln
        115                 120                 125 ctc act gct caa gaa ttg agc aca atg att cgt ctc aag ctg aag ccc    432
Leu Thr Ala Gln Glu Leu Ser Thr Met Ile Arg Leu Lys Leu Lys Pro
    130                 135                 140 atc atc ttt gtc atc tgc aac gat ggc ttt acc att gaa cga ttc att    480
Ile Ile Phe Val Ile Cys Asn Asp Gly Phe Thr Ile Glu Arg Phe Ile
145                 150                 155                 160 cac ggc atg gaa gcc gag tac aac gac atc gca aat tgg gac ttc aag    528
His Gly Met Glu Ala Glu Tyr Asn Asp Ile Ala Asn Trp Asp Phe Lys
                165                 170                 175 gct ctg gtt gac gtc ttt ggc ggc tct aag acg gcc aag aag ttc gcc    576
```

```
Ala Leu Val Asp Val Phe Gly Gly Ser Lys Thr Ala Lys Lys Phe Ala
            180                 185                 190 gtc aag acc aag gac gag ctg gac agc ctt ctc aca gac cct acc ttt      624
Val Lys Thr Lys Asp Glu Leu Asp Ser Leu Leu Thr Asp Pro Thr Phe
        195                 200                 205 aac gcc gca gaa tgc ctc cag ttt gtc gag cta tat atg ccc aaa gaa      672
Asn Ala Ala Glu Cys Leu Gln Phe Val Glu Leu Tyr Met Pro Lys Glu
    210                 215                 220 gat gct                                                               678
Asp Ala
225
```

<210> SEQ ID NO 8
<211> LENGTH: 226
<212> TYPE: PRT
<213> ORGANISM: Unknown
<220> FEATURE:
<223> OTHER INFORMATION: Fungal isolate from soil sample

<400> SEQUENCE: 8

```
Thr Tyr Pro Gly Val Gln Met Arg Gly Val Leu Arg Gln Val Ile Lys
 1               5                  10                  15

Gln Leu Asp Ala Ser Glu Ile Asn Ala Gln Pro Ala Pro Val Val Glu
            20                  25                  30

Asn Glu Val Ala Lys Asn Arg Asp Asn Ser Pro Val Ile Thr Gln Ala
        35                  40                  45

Phe Phe Trp Pro Arg Val Gly Glu Phe Leu Lys Lys Asn Asp Ile Val
    50                  55                  60

Ile Thr Glu Thr Gly Thr Ala Asn Phe Gly Ile Trp Asp Thr Lys Phe
65                  70                  75                  80

Pro Ser Gly Val Thr Ala Leu Ser Gln Val Leu Trp Gly Ser Ile Gly
                85                  90                  95

Trp Ser Val Gly Ala Cys Gln Gly Ala Val Leu Ala Ala Ala Asp Asp
            100                 105                 110

Asn Ser Asp Arg Arg Thr Ile Leu Phe Val Gly Asp Gly Ser Phe Gln
        115                 120                 125

Leu Thr Ala Gln Glu Leu Ser Thr Met Ile Arg Leu Lys Leu Lys Pro
    130                 135                 140

Ile Ile Phe Val Ile Cys Asn Asp Gly Phe Thr Ile Glu Arg Phe Ile
145                 150                 155                 160

His Gly Met Glu Ala Glu Tyr Asn Asp Ile Ala Asn Trp Asp Phe Lys
                165                 170                 175

Ala Leu Val Asp Val Phe Gly Gly Ser Lys Thr Ala Lys Lys Phe Ala
            180                 185                 190

Val Lys Thr Lys Asp Glu Leu Asp Ser Leu Leu Thr Asp Pro Thr Phe
        195                 200                 205

Asn Ala Ala Glu Cys Leu Gln Phe Val Glu Leu Tyr Met Pro Lys Glu
    210                 215                 220

Asp Ala
225
```

<210> SEQ ID NO 9
<211> LENGTH: 1636
<212> TYPE: DNA
<213> ORGANISM: Unknown
<220> FEATURE:
<221> NAME/KEY: CDS
<222> LOCATION: (1)...(1377)
<223> OTHER INFORMATION: Fungal isolate from soil sample

<400> SEQUENCE: 9

```
cga aac ggc atg ctc ctc cac cac acg ctt gga aac ggc gac ttc aac      48
Arg Asn Gly Met Leu Leu His His Thr Leu Gly Asn Gly Asp Phe Asn
  1               5                  10                  15 atc ttt gcc aac atg agc gct caa atc tct tgc gaa gtg gcc aag ctc      96
Ile Phe Ala Asn Met Ser Ala Gln Ile Ser Cys Glu Val Ala Lys Leu
                 20                  25                  30 acc aac cct gcc gaa att gcg acc cag atc gac cat gcc ctc cgc gtt     144
Thr Asn Pro Ala Glu Ile Ala Thr Gln Ile Asp His Ala Leu Arg Val
             35                  40                  45 tgc ttc att cgt tct cgg ccc gtc tac atc atg ctt ccc acc gat atg     192
Cys Phe Ile Arg Ser Arg Pro Val Tyr Ile Met Leu Pro Thr Asp Met
         50                  55                  60 gtc cag gcc aaa gta gaa ggt gcc aga ctc aag gaa cca att gac ttg     240
Val Gln Ala Lys Val Glu Gly Ala Arg Leu Lys Glu Pro Ile Asp Leu
 65                  70                  75                  80 tcg gag cct cca aat gat ccc gag aaa gaa gca tac gtc gtt gac gtt     288
Ser Glu Pro Pro Asn Asp Pro Glu Lys Glu Ala Tyr Val Val Asp Val
                 85                  90                  95 gtc ctc aag tac ctc cgt gct gca aag aac ccc gtc atc ctt gtc gat     336
Val Leu Lys Tyr Leu Arg Ala Ala Lys Asn Pro Val Ile Leu Val Asp
                100                 105                 110 gct tgt gct atc cgt cat cgt gtt ctt gat gag gtt cat gat ctc atc     384
Ala Cys Ala Ile Arg His Arg Val Leu Asp Glu Val His Asp Leu Ile
            115                 120                 125 gaa aag aca aac ctc cct gtc ttt gtc act cct atg ggc aaa ggt gct     432
Glu Lys Thr Asn Leu Pro Val Phe Val Thr Pro Met Gly Lys Gly Ala
        130                 135                 140 gtt aac gaa gaa cac ccg aca tat ggt ggt gtc tat gcc ggt gac ggc     480
Val Asn Glu Glu His Pro Thr Tyr Gly Gly Val Tyr Ala Gly Asp Gly
145                 150                 155                 160 tca cat ccg cct caa gtt aag gac atg gtt gag tct tct gat ttg ata     528
Ser His Pro Pro Gln Val Lys Asp Met Val Glu Ser Ser Asp Leu Ile
                165                 170                 175 ttg aca atc ggt gct ctc aag agc gac ttc aac act gct ggc ttc tct     576
Leu Thr Ile Gly Ala Leu Lys Ser Asp Phe Asn Thr Ala Gly Phe Ser
            180                 185                 190 tac cgt acc tca cag ctg aac acg att gat cta cac agc gac cac tgc     624
Tyr Arg Thr Ser Gln Leu Asn Thr Ile Asp Leu His Ser Asp His Cys
        195                 200                 205 att gtc aaa tac tcg aca tat cca ggt gtc cag atg agg ggt gtg ctg     672
Ile Val Lys Tyr Ser Thr Tyr Pro Gly Val Gln Met Arg Gly Val Leu
    210                 215                 220 cga caa gtg att aag cag ctc gat gca tct gag atc aac gct cag cca     720
Arg Gln Val Ile Lys Gln Leu Asp Ala Ser Glu Ile Asn Ala Gln Pro
225                 230                 235                 240 gcg cca gtc gtc gag aat gaa gtt gcc aaa aac cga gat aac tca ccc     768
Ala Pro Val Val Glu Asn Glu Val Ala Lys Asn Arg Asp Asn Ser Pro
                245                 250                 255 gtc att aca caa gct ttc ttc tgg ccg cgc gtg gga gag ttc ctg aag     816
Val Ile Thr Gln Ala Phe Phe Trp Pro Arg Val Gly Glu Phe Leu Lys
            260                 265                 270 aag aac gac atc gtc att acc gag act gga aca gcc aac ttt ggc atc     864
Lys Asn Asp Ile Val Ile Thr Glu Thr Gly Thr Ala Asn Phe Gly Ile
        275                 280                 285 tgg gat act aag ttt ccc tct ggc gtt act gcg ctt tct cag gtc ctt     912
Trp Asp Thr Lys Phe Pro Ser Gly Val Thr Ala Leu Ser Gln Val Leu
    290                 295                 300
```

```
tgg gga agc att ggt tgg tcc gtt ggt gcc tgc caa gga gcc gtt ctt        960
Trp Gly Ser Ile Gly Trp Ser Val Gly Ala Cys Gln Gly Ala Val Leu
305                 310                 315                 320 gca gcc gcc gat gac aac agc gat cgc aga act atc ctc ttt gtt ggt       1008
Ala Ala Ala Asp Asp Asn Ser Asp Arg Arg Thr Ile Leu Phe Val Gly
                325                 330                 335 gat ggc tca ttc cag ctc act gct caa gaa ttg agc aca atg att cgt       1056
Asp Gly Ser Phe Gln Leu Thr Ala Gln Glu Leu Ser Thr Met Ile Arg
            340                 345                 350 ctc aag ctg aag ccc atc atc ttt gtc atc tgc aac gat ggc ttt acc       1104
Leu Lys Leu Lys Pro Ile Ile Phe Val Ile Cys Asn Asp Gly Phe Thr
        355                 360                 365 att gaa cga ttc att cac ggc atg gaa gcc gag tac aac gac atc gca       1152
Ile Glu Arg Phe Ile His Gly Met Glu Ala Glu Tyr Asn Asp Ile Ala
    370                 375                 380 aat tgg gac ttc aag gct ctg gtt gac gtc ttt ggc ggc tct aag acg       1200
Asn Trp Asp Phe Lys Ala Leu Val Asp Val Phe Gly Gly Ser Lys Thr
385                 390                 395                 400 gcc aag aag ttc gcc gtc aag acc aag gac gag ctg gac agc ctt ctc       1248
Ala Lys Lys Phe Ala Val Lys Thr Lys Asp Glu Leu Asp Ser Leu Leu
                405                 410                 415 aca gac cct acc ttt aac gcc gca gaa tgc ctc cag ttt gtc gag cta       1296
Thr Asp Pro Thr Phe Asn Ala Ala Glu Cys Leu Gln Phe Val Glu Leu
            420                 425                 430 tat atg ccc aaa gaa gat gct cct cga gca ttg atc atg act gca gaa       1344
Tyr Met Pro Lys Glu Asp Ala Pro Arg Ala Leu Ile Met Thr Ala Glu
        435                 440                 445 gct agc gcg agg aac aat gcc aag aca gag taa agtggactgt catgaaggcc    1397
Ala Ser Ala Arg Asn Asn Ala Lys Thr Glu *
450                 455 gatttaccac tcataaatt gtaatagacc tgatacacat agatcaaggc aggtaccgat     1457
cattaatcaa gcaggtttgg atggggaagg attttgaaaa tgaggaaacg atgggatgat    1517
atttggaata actggccatt attttgagta cttataaaca aatttgaagt tcaatttttt    1577
ttcaaaaaaa aaaaaaaaaa aaaaaaaaaa aaaaaaaaaa aaaaaaaaaa aaaaaaaa      1636

<210> SEQ ID NO 10
<211> LENGTH: 1374
<212> TYPE: DNA
<213> ORGANISM: Unknown
<220> FEATURE:
<221> NAME/KEY: CDS
<222> LOCATION: (1)...(1374)
<223> OTHER INFORMATION: Fungal isolate from soil sample

<400> SEQUENCE: 10 cga aac ggc atg ctc ctc cac cac acg ctt gga aac ggc gac ttc aac         48
Arg Asn Gly Met Leu Leu His His Thr Leu Gly Asn Gly Asp Phe Asn
1               5                   10                  15 atc ttt gcc aac atg agc gct caa atc tct tgc gaa gtg gcc aag ctc         96
Ile Phe Ala Asn Met Ser Ala Gln Ile Ser Cys Glu Val Ala Lys Leu
                20                  25                  30 acc aac cct gcc gaa att gcg acc cag atc gac cat gcc ctc cgc gtt        144
Thr Asn Pro Ala Glu Ile Ala Thr Gln Ile Asp His Ala Leu Arg Val
            35                  40                  45 tgc ttc att cgt tct cgg ccc gtc tac atc atg ctt ccc acc gat atg        192
Cys Phe Ile Arg Ser Arg Pro Val Tyr Ile Met Leu Pro Thr Asp Met
    50                  55                  60 gtc cag gcc aaa gta gaa ggt gcc aga ctc aag gaa cca att gac ttg        240
Val Gln Ala Lys Val Glu Gly Ala Arg Leu Lys Glu Pro Ile Asp Leu
65                  70                  75                  80
```

-continued

| | | |
|---|---|---|
| tcg gag cct cca aat gat ccc gag aaa gaa gca tac gtc gtt gac gtt<br>Ser Glu Pro Pro Asn Asp Pro Glu Lys Glu Ala Tyr Val Val Asp Val<br>85 90 95 | 288 | |
| gtc ctc aag tac ctc cgt gct gca aag aac ccc gtc atc ctt gtc gat<br>Val Leu Lys Tyr Leu Arg Ala Ala Lys Asn Pro Val Ile Leu Val Asp<br>100 105 110 | 336 | |
| gct tgt gct atc cgt cat cgt gtt ctt gat gag gtt cat gat ctc atc<br>Ala Cys Ala Ile Arg His Arg Val Leu Asp Glu Val His Asp Leu Ile<br>115 120 125 | 384 | |
| gaa aag aca aac ctc cct gtc ttt gtc act cct atg ggc aaa ggt gct<br>Glu Lys Thr Asn Leu Pro Val Phe Val Thr Pro Met Gly Lys Gly Ala<br>130 135 140 | 432 | |
| gtt aac gaa gaa cac ccg aca tat ggt ggt gtc tat gcc ggt gac ggc<br>Val Asn Glu Glu His Pro Thr Tyr Gly Gly Val Tyr Ala Gly Asp Gly<br>145 150 155 160 | 480 | |
| tca cat ccg cct caa gtt aag gac atg gtt gag tct tct gat ttg ata<br>Ser His Pro Pro Gln Val Lys Asp Met Val Glu Ser Ser Asp Leu Ile<br>165 170 175 | 528 | |
| ttg aca atc ggt gct ctc aag agc gac ttc aac act gct ggc ttc tct<br>Leu Thr Ile Gly Ala Leu Lys Ser Asp Phe Asn Thr Ala Gly Phe Ser<br>180 185 190 | 576 | |
| tac cgt acc tca cag ctg aac acg att gat cta cac agc gac cac tgc<br>Tyr Arg Thr Ser Gln Leu Asn Thr Ile Asp Leu His Ser Asp His Cys<br>195 200 205 | 624 | |
| att gtc aaa tac tcg aca tat cca ggt gtc cag atg agg ggt gtg ctg<br>Ile Val Lys Tyr Ser Thr Tyr Pro Gly Val Gln Met Arg Gly Val Leu<br>210 215 220 | 672 | |
| cga caa gtg att aag cag ctc gat gca tct gag atc aac gct cag cca<br>Arg Gln Val Ile Lys Gln Leu Asp Ala Ser Glu Ile Asn Ala Gln Pro<br>225 230 235 240 | 720 | |
| gcg cca gtc gtc gag aat gaa gtt gcc aaa aac cga gat aac tca ccc<br>Ala Pro Val Val Glu Asn Glu Val Ala Lys Asn Arg Asp Asn Ser Pro<br>245 250 255 | 768 | |
| gtc att aca caa gct ttc ttc tgg ccg cgc gtg gga gag ttc ctg aag<br>Val Ile Thr Gln Ala Phe Phe Trp Pro Arg Val Gly Glu Phe Leu Lys<br>260 265 270 | 816 | |
| aag aac gac atc gtc att acc gag act gga aca gcc aac ttt ggc atc<br>Lys Asn Asp Ile Val Ile Thr Glu Thr Gly Thr Ala Asn Phe Gly Ile<br>275 280 285 | 864 | |
| tgg gat act aag ttt ccc tct ggc gtt act gcg ctt tct cag gtc ctt<br>Trp Asp Thr Lys Phe Pro Ser Gly Val Thr Ala Leu Ser Gln Val Leu<br>290 295 300 | 912 | |
| tgg gga agc att ggt tgg tcc gtt ggt gcc tgc caa gga gcc gtt ctt<br>Trp Gly Ser Ile Gly Trp Ser Val Gly Ala Cys Gln Gly Ala Val Leu<br>305 310 315 320 | 960 | |
| gca gcc gcc gat gac aac agc gat cgc aga act atc ctc ttt gtt ggt<br>Ala Ala Ala Asp Asp Asn Ser Asp Arg Arg Thr Ile Leu Phe Val Gly<br>325 330 335 | 1008 | |
| gat ggc tca ttc cag ctc act gct caa gaa ttg agc aca atg att cgt<br>Asp Gly Ser Phe Gln Leu Thr Ala Gln Glu Leu Ser Thr Met Ile Arg<br>340 345 350 | 1056 | |
| ctc aag ctg aag ccc atc atc ttt gtc atc tgc aac gat ggc ttt acc<br>Leu Lys Leu Lys Pro Ile Ile Phe Val Ile Cys Asn Asp Gly Phe Thr<br>355 360 365 | 1104 | |
| att gaa cga ttc att cac ggc atg gaa gcc gag tac aac gac atc gca<br>Ile Glu Arg Phe Ile His Gly Met Glu Ala Glu Tyr Asn Asp Ile Ala<br>370 375 380 | 1152 | |
| aat tgg gac ttc aag gct ctg gtt gac gtc ttt ggc ggc tct aag acg<br>Asn Trp Asp Phe Lys Ala Leu Val Asp Val Phe Gly Gly Ser Lys Thr | 1200 | |

-continued

```
                385                 390                 395                 400
gcc aag aag ttc gcc gtc aag acc aag gac gag ctg gac agc ctt ctc      1248
Ala Lys Lys Phe Ala Val Lys Thr Lys Asp Glu Leu Asp Ser Leu Leu
                405                 410                 415 aca gac cct acc ttt aac gcc gca gaa tgc ctc cag ttt gtc gag cta      1296
Thr Asp Pro Thr Phe Asn Ala Ala Glu Cys Leu Gln Phe Val Glu Leu
            420                 425                 430 tat atg ccc aaa gaa gat gct cct cga gca ttg atc atg act gca gaa      1344
Tyr Met Pro Lys Glu Asp Ala Pro Arg Ala Leu Ile Met Thr Ala Glu
        435                 440                 445 gct agc gcg agg aac aat gcc aag aca gag                              1374
Ala Ser Ala Arg Asn Asn Ala Lys Thr Glu
    450                 455

<210> SEQ ID NO 11
<211> LENGTH: 458
<212> TYPE: PRT
<213> ORGANISM: Unknown
<220> FEATURE:
<223> OTHER INFORMATION: Fungal isolate from soil sample

<400> SEQUENCE: 11

Arg Asn Gly Met Leu His His Thr Leu Gly Asn Gly Asp Phe Asn
1               5                   10                  15

Ile Phe Ala Asn Met Ser Ala Gln Ile Ser Cys Glu Val Ala Lys Leu
            20                  25                  30

Thr Asn Pro Ala Glu Ile Ala Thr Gln Ile Asp His Ala Leu Arg Val
        35                  40                  45

Cys Phe Ile Arg Ser Arg Pro Val Tyr Ile Met Leu Pro Thr Asp Met
    50                  55                  60

Val Gln Ala Lys Val Glu Gly Ala Arg Leu Lys Glu Pro Ile Asp Leu
65                  70                  75                  80

Ser Glu Pro Pro Asn Asp Pro Glu Lys Glu Ala Tyr Val Val Asp Val
                85                  90                  95

Val Leu Lys Tyr Leu Arg Ala Ala Lys Asn Pro Val Ile Leu Val Asp
            100                 105                 110

Ala Cys Ala Ile Arg His Arg Val Leu Asp Glu Val His Asp Leu Ile
        115                 120                 125

Glu Lys Thr Asn Leu Pro Val Phe Val Thr Pro Met Gly Lys Gly Ala
    130                 135                 140

Val Asn Glu Glu His Pro Thr Tyr Gly Gly Val Tyr Ala Gly Asp Gly
145                 150                 155                 160

Ser His Pro Pro Gln Val Lys Asp Met Val Glu Ser Ser Asp Leu Ile
                165                 170                 175

Leu Thr Ile Gly Ala Leu Lys Ser Asp Phe Asn Thr Ala Gly Phe Ser
            180                 185                 190

Tyr Arg Thr Ser Gln Leu Asn Thr Ile Asp Leu His Ser Asp His Cys
        195                 200                 205

Ile Val Lys Tyr Ser Thr Tyr Pro Gly Val Gln Met Arg Gly Val Leu
    210                 215                 220

Arg Gln Val Ile Lys Gln Leu Asp Ala Ser Glu Ile Asn Ala Gln Pro
225                 230                 235                 240

Ala Pro Val Val Glu Asn Glu Val Ala Lys Asn Arg Asp Asn Ser Pro
                245                 250                 255

Val Ile Thr Gln Ala Phe Phe Trp Pro Arg Val Gly Glu Phe Leu Lys
            260                 265                 270
```

```
Lys Asn Asp Ile Val Ile Thr Glu Thr Gly Thr Ala Asn Phe Gly Ile
        275                 280                 285

Trp Asp Thr Lys Phe Pro Ser Gly Val Thr Ala Leu Ser Gln Val Leu
    290                 295                 300

Trp Gly Ser Ile Gly Trp Ser Val Gly Ala Cys Gln Gly Ala Val Leu
305                 310                 315                 320

Ala Ala Ala Asp Asp Asn Ser Asp Arg Arg Thr Ile Leu Phe Val Gly
                325                 330                 335

Asp Gly Ser Phe Gln Leu Thr Ala Gln Glu Leu Ser Thr Met Ile Arg
            340                 345                 350

Leu Lys Leu Lys Pro Ile Ile Phe Val Ile Cys Asn Asp Gly Phe Thr
        355                 360                 365

Ile Glu Arg Phe Ile His Gly Met Glu Ala Glu Tyr Asn Asp Ile Ala
    370                 375                 380

Asn Trp Asp Phe Lys Ala Leu Val Asp Val Phe Gly Gly Ser Lys Thr
385                 390                 395                 400

Ala Lys Lys Phe Ala Val Lys Thr Lys Asp Glu Leu Asp Ser Leu Leu
                405                 410                 415

Thr Asp Pro Thr Phe Asn Ala Ala Glu Cys Leu Gln Phe Val Glu Leu
            420                 425                 430

Tyr Met Pro Lys Glu Asp Ala Pro Arg Ala Leu Ile Met Thr Ala Glu
        435                 440                 445

Ala Ser Ala Arg Asn Asn Ala Lys Thr Glu
    450                 455

<210> SEQ ID NO 12
<211> LENGTH: 30
<212> TYPE: DNA
<213> ORGANISM: Unknown
<220> FEATURE:
<221> NAME/KEY: CDS
<222> LOCATION: (1)...(30)
<223> OTHER INFORMATION: Oligonucleotide used for PCR amplification of
      GDC-1

<400> SEQUENCE: 12 tcc cag atg cca aag ttg gct gtt cca gtc                              30
Ser Gln Met Pro Lys Leu Ala Val Pro Val
1               5                   10

<210> SEQ ID NO 13
<211> LENGTH: 563
<212> TYPE: PRT
<213> ORGANISM: Saccharomyces cerevisiae

<400> SEQUENCE: 13

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Arg Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95
```

```
His Val Val Gly Val Pro Ser Ile Ser Ser Gln Ala Lys Gln Leu Leu
                100                 105                 110
Leu His His Thr Leu Gly Asn Gly Asp Phe Thr Val Phe His Arg Met
            115                 120                 125
Ser Ala Asn Ile Ser Glu Thr Thr Ala Met Ile Thr Asp Ile Cys Thr
130                 135                 140
Ala Pro Ala Glu Ile Asp Arg Cys Ile Arg Thr Thr Tyr Val Thr Gln
145                 150                 155                 160
Arg Pro Val Tyr Leu Gly Leu Pro Ala Asn Leu Val Asp Leu Asn Val
                165                 170                 175
Pro Ala Lys Leu Leu Gln Thr Pro Ile Asp Met Ser Leu Lys Pro Asn
                180                 185                 190
Asp Ala Glu Ser Glu Lys Glu Val Ile Asp Thr Ile Leu Val Leu Ala
                195                 200                 205
Lys Asp Ala Lys Asn Pro Val Ile Leu Ala Asp Ala Cys Cys Ser Arg
210                 215                 220
His Asp Val Lys Ala Glu Thr Lys Lys Leu Ile Asp Leu Thr Gln Phe
225                 230                 235                 240
Pro Ala Phe Val Thr Pro Met Gly Lys Gly Ser Ile Ser Glu Gln His
                245                 250                 255
Pro Arg Tyr Gly Gly Val Tyr Val Gly Thr Leu Ser Lys Pro Glu Val
                260                 265                 270
Lys Glu Ala Val Glu Ser Ala Asp Leu Ile Leu Ser Val Gly Ala Leu
                275                 280                 285
Leu Ser Asp Phe Asn Thr Gly Ser Phe Ser Tyr Ser Tyr Lys Thr Lys
                290                 295                 300
Asn Ile Val Glu Phe His Ser Asp His Met Lys Ile Arg Asn Ala Thr
305                 310                 315                 320
Phe Pro Gly Val Gln Met Lys Phe Val Leu Gln Lys Leu Leu Thr Asn
                325                 330                 335
Ile Ala Asp Ala Ala Lys Gly Tyr Lys Pro Val Ala Val Pro Ala Arg
                340                 345                 350
Thr Pro Ala Asn Ala Ala Val Pro Ala Ser Thr Pro Leu Lys Gln Glu
                355                 360                 365
Trp Met Trp Asn Gln Leu Gly Asn Phe Leu Gln Glu Gly Asp Val Val
                370                 375                 380
Ile Ala Glu Thr Gly Thr Ser Ala Phe Gly Ile Asn Gln Thr Thr Phe
385                 390                 395                 400
Pro Asn Asn Thr Tyr Gly Ile Ser Gln Val Leu Trp Gly Ser Ile Gly
                405                 410                 415
Phe Thr Thr Gly Ala Thr Leu Gly Ala Ala Phe Ala Ala Glu Glu Ile
                420                 425                 430
Asp Pro Lys Lys Arg Val Ile Leu Phe Ile Gly Asp Gly Ser Leu Gln
                435                 440                 445
Leu Thr Val Gln Glu Ile Ser Thr Met Ile Arg Trp Gly Leu Lys Pro
                450                 455                 460
Tyr Leu Phe Val Leu Asn Asn Asp Gly Tyr Thr Ile Glu Lys Leu Ile
465                 470                 475                 480
His Gly Pro Lys Ala Gln Tyr Asn Glu Ile Gln Gly Trp Asp His Leu
                485                 490                 495
Ser Leu Leu Pro Thr Phe Gly Ala Lys Asp Tyr Glu Thr His Arg Val
                500                 505                 510
Ala Thr Thr Gly Glu Trp Asp Lys Leu Thr Gln Asp Lys Ser Phe Asn
```

```
                    515                 520                 525
Asp Asn Ser Lys Ile Arg Met Ile Glu Val Met Leu Pro Val Phe Asp
                530                 535                 540

Ala Pro Gln Asn Leu Val Glu Gln Ala Lys Leu Thr Ala Ala Thr Asn
545                 550                 555                 560

Ala Lys Gln

<210> SEQ ID NO 14
<211> LENGTH: 550
<212> TYPE: PRT
<213> ORGANISM: Salmonella typhimurium

<400> SEQUENCE: 14

Met Gln Asn Pro Tyr Thr Val Ala Asp Tyr Leu Leu Asp Arg Leu Ala
  1               5                  10                  15

Gly Cys Gly Ile Gly His Leu Phe Gly Val Pro Gly Asp Tyr Asn Leu
                 20                  25                  30

Gln Phe Leu Asp His Val Ile Asp His Pro Thr Leu Arg Trp Val Gly
             35                  40                  45

Cys Ala Asn Glu Leu Asn Ala Ala Tyr Ala Ala Asp Gly Tyr Ala Arg
         50                  55                  60

Met Ser Gly Ala Gly Ala Leu Leu Thr Thr Phe Gly Val Gly Glu Leu
 65                  70                  75                  80

Ser Ala Ile Asn Gly Ile Ala Gly Ser Tyr Ala Glu Tyr Val Pro Val
                 85                  90                  95

Leu His Ile Val Gly Ala Pro Cys Ser Ala Ala Gln Gln Arg Gly Glu
            100                 105                 110

Leu Met His His Thr Leu Gly Asp Gly Asp Phe Arg His Phe Tyr Arg
            115                 120                 125

Met Ser Gln Ala Ile Ser Ala Ala Ser Ala Ile Leu Asp Glu Gln Asn
130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
            180                 185                 190

Gly Val Glu Thr Ala Phe Arg Tyr His Ala Arg Gln Cys Leu Met Asn
            195                 200                 205

Ser Arg Arg Ile Ala Leu Leu Ala Asp Phe Leu Ala Gly Arg Phe Gly
210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
            275                 280                 285

Asp Thr Leu Thr Ala Gly Phe Thr Gln Gln Leu Pro Ala Glu Arg Thr
290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
```

```
            325                 330                 335
Cys Ala Phe Ala Pro Pro Thr Arg Ser Ala Gly Gln Pro Val Arg
            340                 345                 350

Ile Asp Lys Gly Glu Leu Thr Gln Glu Ser Phe Trp Gln Thr Leu Gln
        355                 360                 365

Gln Tyr Leu Lys Pro Gly Asp Ile Ile Leu Val Asp Gln Gly Thr Ala
    370                 375                 380

Ala Phe Gly Ala Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
            420                 425                 430

Asp Gly Ala Ala Gln Leu Thr Ile Gln Glu Met Gly Ser Met Leu Arg
        435                 440                 445

Asp Gly Gln Ala Pro Val Ile Leu Leu Leu Asn Asn Asp Gly Tyr Thr
    450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
            500                 505                 510

Glu Arg Leu Ala Arg Pro Gln Arg Leu Ser Phe Ile Glu Val Met Leu
        515                 520                 525

Pro Lys Ala Asp Leu Pro Glu Leu Leu Arg Thr Val Thr Arg Ala Leu
    530                 535                 540

Glu Ala Arg Asn Gly Gly
545                 550

<210> SEQ ID NO 15
<211> LENGTH: 568
<212> TYPE: PRT
<213> ORGANISM: Zymomonas mobilis

<400> SEQUENCE: 15

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala His Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140
```

-continued

```
Pro Ala Lys Ile Asp His Val Ile Lys Thr Ala Leu Ala Lys Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Asp Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Thr Asp Ala Leu Gly Gly Ala Val
225                 230                 235                 240

Ala Thr Met Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
                260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Arg Arg Ile Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ser Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Ala Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
```

<210> SEQ ID NO 16
<211> LENGTH: 687
<212> TYPE: PRT
<213> ORGANISM: Saccharomyces cerevisiae

<400> SEQUENCE: 16

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285

Ile Asn Lys Ala Ala Asp Leu Ile Asn Leu Ala Lys Lys Pro Val Leu
290                 295                 300

Tyr Val Gly Ala Gly Ile Leu Asn His Ala Asp Gly Pro Arg Leu Leu
305                 310                 315                 320

Lys Glu Leu Ser Asp Arg Ala Gln Ile Pro Val Thr Thr Thr Leu Gln
                325                 330                 335

Gly Leu Gly Ser Phe Asp Gln Glu Asp Pro Lys Ser Leu Asp Met Leu
            340                 345                 350

Gly Met His Gly Cys Ala Thr Ala Asn Leu Ala Val Gln Asn Ala Asp
        355                 360                 365

```
Leu Ile Ile Ala Val Gly Ala Arg Phe Asp Asp Arg Val Thr Gly Asn
    370                 375                 380

Ile Ser Lys Phe Ala Pro Glu Ala Arg Arg Ala Ala Ala Glu Gly Arg
385                 390                 395                 400

Gly Gly Ile Ile His Phe Glu Val Ser Pro Lys Asn Ile Asn Lys Val
                405                 410                 415

Val Gln Thr Gln Ile Ala Val Glu Gly Asp Ala Thr Thr Asn Leu Gly
            420                 425                 430

Lys Met Met Ser Lys Ile Phe Pro Val Lys Glu Arg Ser Glu Trp Phe
        435                 440                 445

Ala Gln Ile Asn Lys Trp Lys Lys Glu Tyr Pro Tyr Ala Tyr Met Glu
    450                 455                 460

Glu Thr Pro Gly Ser Lys Ile Lys Pro Gln Thr Val Ile Lys Lys Leu
465                 470                 475                 480

Ser Lys Val Ala Asn Asp Thr Gly Arg His Val Ile Val Thr Thr Gly
                485                 490                 495

Val Gly Gln His Gln Met Trp Ala Ala Gln His Trp Thr Trp Arg Asn
            500                 505                 510

Pro His Thr Phe Ile Thr Ser Gly Gly Leu Gly Thr Met Gly Tyr Gly
        515                 520                 525

Leu Pro Ala Ala Ile Gly Ala Gln Val Ala Lys Pro Glu Ser Leu Val
    530                 535                 540

Ile Asp Ile Asp Gly Asp Ala Ser Phe Asn Met Thr Leu Thr Glu Leu
545                 550                 555                 560

Ser Ser Ala Val Gln Ala Gly Thr Pro Val Lys Ile Leu Ile Leu Asn
                565                 570                 575

Asn Glu Glu Gln Gly Met Val Thr Gln Trp Gln Ser Leu Phe Tyr Glu
            580                 585                 590

His Arg Tyr Ser His Thr His Gln Leu Asn Pro Asp Phe Ile Lys Leu
        595                 600                 605

Ala Glu Ala Met Gly Leu Lys Gly Leu Arg Val Lys Lys Gln Glu Glu
    610                 615                 620

Leu Asp Ala Lys Leu Lys Glu Phe Val Ser Thr Lys Gly Pro Val Leu
625                 630                 635                 640

Leu Glu Val Glu Val Asp Lys Lys Val Pro Val Leu Pro Met Val Ala
                645                 650                 655

Gly Gly Ser Gly Leu Asp Glu Phe Ile Asn Phe Asp Pro Glu Val Glu
            660                 665                 670

Arg Gln Gln Thr Glu Leu Arg His Lys Arg Thr Gly Lys His
        675                 680                 685

<210> SEQ ID NO 17
<211> LENGTH: 686
<212> TYPE: PRT
<213> ORGANISM: Magnaporthe grisea

<400> SEQUENCE: 17

Met Leu Arg Thr Val Gly Arg Lys Ala Leu Arg Gly Ser Ser Lys Gly
1               5                   10                  15

Cys Ser Arg Thr Ile Ser Thr Leu Lys Pro Ala Thr Ala Thr Ile Ala
            20                  25                  30

Lys Pro Gly Ser Arg Thr Leu Ser Thr Pro Ala Thr Ala Thr Ala Thr
        35                  40                  45

Ala Pro Arg Thr Lys Pro Ser Ala Ser Phe Asn Ala Arg Arg Asp Pro
    50                  55                  60
```

```
Gln Pro Leu Val Asn Pro Arg Ser Gly Glu Ala Asp Glu Ser Phe Ile
 65                  70                  75                  80

Gly Lys Thr Gly Gly Glu Ile Phe His Glu Met Met Leu Arg Gln Asn
                 85                  90                  95

Val Lys His Ile Phe Gly Tyr Pro Gly Ala Ile Leu Pro Val Phe
            100                 105                 110

Asp Ala Ile Tyr Asn Ser Lys His Ile Asp Phe Val Leu Pro Lys His
            115                 120                 125

Glu Gln Gly Ala Gly His Met Ala Glu Gly Tyr Ala Arg Ala Ser Gly
            130                 135                 140

Lys Pro Gly Val Val Leu Val Thr Ser Gly Pro Gly Ala Thr Asn Val
145                 150                 155                 160

Ile Thr Pro Met Ala Asp Ala Leu Ala Asp Gly Thr Pro Leu Val Val
                165                 170                 175

Phe Ser Gly Gln Val Val Thr Ser Asp Ile Gly Ser Asp Ala Phe Gln
            180                 185                 190

Glu Ala Asp Val Ile Gly Ile Ser Arg Ser Cys Thr Lys Trp Asn Val
            195                 200                 205

Met Val Lys Ser Ala Asp Glu Leu Pro Arg Arg Ile Asn Glu Ala Phe
210                 215                 220

Glu Ile Ala Thr Ser Gly Arg Pro Gly Pro Val Leu Val Asp Pro Ala
225                 230                 235                 240

Lys Asp Val Thr Ala Ser Val Leu Arg Arg Ala Ile Pro Thr Glu Thr
                245                 250                 255

Ser Ile Pro Ser Ile Ser Ala Ala Arg Ala Val Gln Glu Ala Gly
            260                 265                 270

Arg Lys Gln Leu Glu His Ser Ile Lys Arg Val Ala Asp Leu Val Asn
            275                 280                 285

Ile Ala Lys Lys Pro Val Ile Tyr Ala Gly Gln Gly Val Ile Leu Ser
290                 295                 300

Glu Gly Gly Val Glu Leu Leu Lys Ala Leu Ala Asp Lys Ala Ser Ile
305                 310                 315                 320

Pro Val Thr Thr Thr Leu His Gly Leu Gly Ala Phe Asp Glu Leu Asp
                325                 330                 335

Glu Lys Ala Leu His Met Leu Gly Met His Gly Ser Ala Tyr Ala Asn
            340                 345                 350

Met Ser Met Gln Glu Ala Asp Leu Ile Ile Ala Leu Gly Gly Arg Phe
            355                 360                 365

Asp Asp Arg Val Thr Gly Ser Ile Pro Lys Phe Ala Pro Ala Ala Lys
370                 375                 380

Leu Ala Ala Ala Glu Gly Arg Gly Gly Ile Val His Phe Glu Ile Met
385                 390                 395                 400

Pro Lys Asn Ile Asn Lys Val Val Gln Ala Thr Glu Ala Ile Glu Gly
                405                 410                 415

Asp Val Ala Ser Asn Leu Lys Leu Leu Leu Pro Lys Ile Glu Gln Arg
            420                 425                 430

Ser Met Thr Asp Arg Lys Glu Trp Phe Asp Gln Ile Lys Glu Trp Lys
            435                 440                 445

Glu Lys Trp Pro Leu Ser His Tyr Glu Arg Ala Glu Arg Ser Gly Leu
            450                 455                 460

Ile Lys Pro Gln Thr Leu Ile Glu Glu Leu Ser Asn Leu Thr Ala Asp
465                 470                 475                 480
```

```
Arg Lys Asp Met Thr Tyr Ile Thr Thr Gly Val Gly Gln His Gln Met
                485                 490                 495

Trp Thr Ala Gln His Phe Arg Trp Arg His Pro Arg Ser Met Ile Thr
            500                 505                 510

Ser Gly Gly Leu Gly Thr Met Gly Tyr Gly Leu Pro Ala Ala Ile Gly
        515                 520                 525

Ala Lys Val Ala Arg Pro Asp Ala Leu Val Ile Asp Ile Asp Gly Asp
    530                 535                 540

Ala Ser Phe Asn Met Thr Leu Thr Glu Leu Ser Thr Ala Ala Gln Phe
545                 550                 555                 560

Asn Ile Gly Val Lys Val Ile Val Leu Asn Asn Glu Glu Gln Gly Met
                565                 570                 575

Val Thr Gln Trp Gln Asn Leu Phe Tyr Glu Asp Arg Tyr Ser His Thr
            580                 585                 590

His Gln Arg Asn Pro Asp Phe Met Lys Leu Ala Asp Ala Met Asp Val
        595                 600                 605

Gln His Arg Arg Val Ser Lys Pro Asp Asp Val Gly Asp Ala Leu Thr
    610                 615                 620

Trp Leu Ile Asn Thr Asp Gly Pro Ala Leu Leu Glu Val Met Thr Asp
625                 630                 635                 640

Lys Lys Val Pro Val Leu Pro Met Val Pro Gly Gly Asn Gly Leu His
                645                 650                 655

Glu Phe Ile Thr Phe Asp Ala Ser Lys Asp Lys Gln Arg Arg Glu Leu
            660                 665                 670

Met Arg Ala Arg Thr Asn Gly Leu His Gly Arg Thr Ala Val
        675                 680                 685

<210> SEQ ID NO 18
<211> LENGTH: 1728
<212> TYPE: DNA
<213> ORGANISM: Unknown
<220> FEATURE:
<223> OTHER INFORMATION: Fungal isolate from soil sample
<220> FEATURE:
<221> NAME/KEY: CDS
<222> LOCATION: (1)...(1728)

<400> SEQUENCE: 18 atg gcc agc atc aac atc agg gtg cag aat ctc gag caa ccc atg gac      48
Met Ala Ser Ile Asn Ile Arg Val Gln Asn Leu Glu Gln Pro Met Asp
 1               5                  10                  15 gtt gcc gag tat ctt ttc cgg cgt ctc cac gaa atc ggc att cgc tcc      96
Val Ala Glu Tyr Leu Phe Arg Arg Leu His Glu Ile Gly Ile Arg Ser
                20                  25                  30 atc cac ggt ctt cca ggc gat tac aac cct ctt gcc ctc gac tat ttg     144
Ile His Gly Leu Pro Gly Asp Tyr Asn Pro Leu Ala Leu Asp Tyr Leu
            35                  40                  45 cca tca tgt ggc ctg aga tgg gtt ggc agc gtc aac gaa ctc aat gct     192
Pro Ser Cys Gly Leu Arg Trp Val Gly Ser Val Asn Glu Leu Asn Ala
        50                  55                  60 gct tat gct gct gat ggc tat gcc cgc gtc aag cag atg gga gct ctc     240
Ala Tyr Ala Ala Asp Gly Tyr Ala Arg Val Lys Gln Met Gly Ala Leu
65                  70                  75                  80 atc acc act ttt gga gtg gga gag ctc tca gcc atc aat ggc gtt gcc     288
Ile Thr Thr Phe Gly Val Gly Glu Leu Ser Ala Ile Asn Gly Val Ala
                85                  90                  95 ggt gcc ttt tcg gaa cac gtc cca gtc gtt cac att gtt ggc tgc cct     336
Gly Ala Phe Ser Glu His Val Pro Val Val His Ile Val Gly Cys Pro
                100                 105                 110
```

```
tcc act gcc tcg cag cga aac ggc atg ctc ctc cac cac acg ctt gga    384
Ser Thr Ala Ser Gln Arg Asn Gly Met Leu Leu His His Thr Leu Gly
        115                 120                 125 aac ggc gac ttc aac atc ttt gcc aac atg agc gct caa atc tct tgc    432
Asn Gly Asp Phe Asn Ile Phe Ala Asn Met Ser Ala Gln Ile Ser Cys
    130                 135                 140 gaa gtg gcc aag ctc acc aac cct gcc gaa att gcg acc cag atc gac    480
Glu Val Ala Lys Leu Thr Asn Pro Ala Glu Ile Ala Thr Gln Ile Asp
145                 150                 155                 160 cat gcc ctc cgc gtt tgc ttc att cgt tct cgg ccc gtc tac atc atg    528
His Ala Leu Arg Val Cys Phe Ile Arg Ser Arg Pro Val Tyr Ile Met
                165                 170                 175 ctt ccc acc gat atg gtc cag gcc aaa gta gaa ggt gcc aga ctc aag    576
Leu Pro Thr Asp Met Val Gln Ala Lys Val Glu Gly Ala Arg Leu Lys
            180                 185                 190 gaa cca att gac ttg tcg gag cct cca aat gat ccc gag aaa gaa gca    624
Glu Pro Ile Asp Leu Ser Glu Pro Pro Asn Asp Pro Glu Lys Glu Ala
        195                 200                 205 tac gtc gtt gac gtt gtc ctc aag tac ctc cgt gct gca aag aac ccc    672
Tyr Val Val Asp Val Val Leu Lys Tyr Leu Arg Ala Ala Lys Asn Pro
    210                 215                 220 gtc atc ctt gtc gat gct tgt gct atc cgt cat cgt gtt ctt gat gag    720
Val Ile Leu Val Asp Ala Cys Ala Ile Arg His Arg Val Leu Asp Glu
225                 230                 235                 240 gtt cat gat ctc atc gaa aag aca aac ctc ccc gtc ttt gtc act cct    768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc    816
Met Gly Lys Gly Ala Val Asn Glu Glu His Pro Thr Tyr Gly Gly Val
            260                 265                 270 tat gcc ggt gac ggc tca cat ccg cct caa gtt aag gac atg gtt gag    864
Tyr Ala Gly Asp Gly Ser His Pro Pro Gln Val Lys Asp Met Val Glu
        275                 280                 285 tct tct gat ttg ata ttg aca atc ggt gct ctc aag agc gac ttc aac    912
Ser Ser Asp Leu Ile Leu Thr Ile Gly Ala Leu Lys Ser Asp Phe Asn
    290                 295                 300 act gct ggc ttc tct tac cgt acc tca cag ctg aac acg att gat cta    960
Thr Ala Gly Phe Ser Tyr Arg Thr Ser Gln Leu Asn Thr Ile Asp Leu
305                 310                 315                 320 cac agc gac cac tgc att gtc aaa tac tcg aca tat cca ggt gtc cag   1008
His Ser Asp His Cys Ile Val Lys Tyr Ser Thr Tyr Pro Gly Val Gln
                325                 330                 335 atg agg ggt gtg ctg cga caa gtg att aag cag ctc gat gca tct gag   1056
Met Arg Gly Val Leu Arg Gln Val Ile Lys Gln Leu Asp Ala Ser Glu
            340                 345                 350 atc aac gct cag cca gcg cca gtc gtc gag aat gaa gtt gcc aaa aac   1104
Ile Asn Ala Gln Pro Ala Pro Val Val Glu Asn Glu Val Ala Lys Asn
        355                 360                 365 cga gat aac tca ccc gtc att aca caa gct ttc ttc tgg ccg cgc gtg   1152
Arg Asp Asn Ser Pro Val Ile Thr Gln Ala Phe Phe Trp Pro Arg Val
    370                 375                 380 gga gag ttc ctg aag aag aac gac atc gtc att acc gag act gga aca   1200
Gly Glu Phe Leu Lys Lys Asn Asp Ile Val Ile Thr Glu Thr Gly Thr
385                 390                 395                 400 gcc aac ttt ggc atc tgg gat act aag ttt ccc tct ggc gtt act gcg   1248
Ala Asn Phe Gly Ile Trp Asp Thr Lys Phe Pro Ser Gly Val Thr Ala
                405                 410                 415 ctt tct cag gtc ctt tgg gga agc att ggt tgg tcc gtt ggt gcc tgc   1296
Leu Ser Gln Val Leu Trp Gly Ser Ile Gly Trp Ser Val Gly Ala Cys
```

-continued

```
                     420                 425                 430
caa gga gcc gtt ctt gca gcc gcc gat gac aac agc gat cgc aga act     1344
Gln Gly Ala Val Leu Ala Ala Ala Asp Asp Asn Ser Asp Arg Arg Thr
            435                 440                 445 atc ctc ttt gtt ggt gat ggc tca ttc cag ctc act gct caa gaa ttg     1392
Ile Leu Phe Val Gly Asp Gly Ser Phe Gln Leu Thr Ala Gln Glu Leu
    450                 455                 460 agc aca atg att cgt ctc aag ctg aag ccc atc atc ttt gtc atc tgc     1440
Ser Thr Met Ile Arg Leu Lys Leu Lys Pro Ile Ile Phe Val Ile Cys
465                 470                 475                 480 aac gat ggc ttt acc att gaa cga ttc att cac ggc atg gaa gcc gag     1488
Asn Asp Gly Phe Thr Ile Glu Arg Phe Ile His Gly Met Glu Ala Glu
                485                 490                 495 tac aac gac atc gca aat tgg gac ttc aag gct ctg gtt gac gtc ttt     1536
Tyr Asn Asp Ile Ala Asn Trp Asp Phe Lys Ala Leu Val Asp Val Phe
            500                 505                 510 ggc ggc tct aag acg gcc aag aag ttc gcc gtc aag acc aag gac gag     1584
Gly Gly Ser Lys Thr Ala Lys Lys Phe Ala Val Lys Thr Lys Asp Glu
    515                 520                 525 ctg gac agc ctt ctc aca gac cct acc ttt aac gcc gca gaa tgc ctc     1632
Leu Asp Ser Leu Leu Thr Asp Pro Thr Phe Asn Ala Ala Glu Cys Leu
530                 535                 540 cag ttt gtc gag cta tat atg ccc aaa gaa gat gct cct cga gca ttg     1680
Gln Phe Val Glu Leu Tyr Met Pro Lys Glu Asp Ala Pro Arg Ala Leu
545                 550                 555                 560 atc atg acg gca gaa gct agc gcg agg aac aat gcc aag aca gag taa     1728
Ile Met Thr Ala Glu Ala Ser Ala Arg Asn Asn Ala Lys Thr Glu *
                565                 570                 575
```

<210> SEQ ID NO 19
<211> LENGTH: 575
<212> TYPE: PRT
<213> ORGANISM: Unknown
<220> FEATURE:
<223> OTHER INFORMATION: Fungal isolate from soil sample

<400> SEQUENCE: 19

```
Met Ala Ser Ile Asn Ile Arg Val Gln Asn Leu Glu Gln Pro Met Asp
1               5                   10                  15

Val Ala Glu Tyr Leu Phe Arg Arg Leu His Glu Ile Gly Ile Arg Ser
            20                  25                  30

Ile His Gly Leu Pro Gly Asp Tyr Asn Pro Leu Ala Leu Asp Tyr Leu
        35                  40                  45

Pro Ser Cys Gly Leu Arg Trp Val Gly Ser Val Asn Glu Leu Asn Ala
    50                  55                  60

Ala Tyr Ala Ala Asp Gly Tyr Ala Arg Val Lys Gln Met Gly Ala Leu
65                  70                  75                  80

Ile Thr Thr Phe Gly Val Gly Glu Leu Ser Ala Ile Asn Gly Val Ala
                85                  90                  95

Gly Ala Phe Ser Glu His Val Pro Val Val His Ile Val Gly Cys Pro
            100                 105                 110

Ser Thr Ala Ser Gln Arg Asn Gly Met Leu Leu His Thr Leu Gly
        115                 120                 125

Asn Gly Asp Phe Asn Ile Phe Ala Asn Met Ser Ala Gln Ile Ser Cys
    130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
```

-continued

```
                165                 170                 175
Leu Pro Thr Asp Met Val Gln Ala Lys Val Glu Gly Ala Arg Leu Lys
            180                 185                 190
Glu Pro Ile Asp Leu Ser Glu Pro Pro Asn Asp Pro Glu Lys Glu Ala
        195                 200                 205
Tyr Val Asp Val Val Leu Lys Tyr Leu Arg Ala Ala Lys Asn Pro
    210                 215                 220
Val Ile Leu Val Asp Ala Cys Ala Ile Arg His Arg Val Leu Asp Glu
225                 230                 235                 240
Val His Asp Leu Ile Glu Lys Thr Asn Leu Pro Val Phe Val Thr Pro
                245                 250                 255
Met Gly Lys Gly Ala Val Asn Glu Glu His Pro Thr Tyr Gly Gly Val
            260                 265                 270
Tyr Ala Gly Asp Gly Ser His Pro Pro Gln Val Lys Asp Met Val Glu
        275                 280                 285
Ser Ser Asp Leu Ile Leu Thr Ile Gly Ala Leu Lys Ser Asp Phe Asn
    290                 295                 300
Thr Ala Gly Phe Ser Tyr Arg Thr Ser Gln Leu Asn Thr Ile Asp Leu
305                 310                 315                 320
His Ser Asp His Cys Ile Val Lys Tyr Ser Thr Tyr Pro Gly Val Gln
                325                 330                 335
Met Arg Gly Val Leu Arg Gln Val Ile Lys Gln Leu Asp Ala Ser Glu
            340                 345                 350
Ile Asn Ala Gln Pro Ala Pro Val Val Glu Asn Glu Val Ala Lys Asn
        355                 360                 365
Arg Asp Asn Ser Pro Val Ile Thr Gln Ala Phe Phe Trp Pro Arg Val
    370                 375                 380
Gly Glu Phe Leu Lys Lys Asn Asp Ile Val Ile Thr Glu Thr Gly Thr
385                 390                 395                 400
Ala Asn Phe Gly Ile Trp Asp Thr Lys Phe Pro Ser Gly Val Thr Ala
                405                 410                 415
Leu Ser Gln Val Leu Trp Gly Ser Ile Gly Trp Ser Val Gly Ala Cys
            420                 425                 430
Gln Gly Ala Val Leu Ala Ala Asp Asp Asn Ser Asp Arg Arg Thr
        435                 440                 445
Ile Leu Phe Val Gly Asp Gly Ser Phe Gln Leu Thr Ala Gln Glu Leu
    450                 455                 460
Ser Thr Met Ile Arg Leu Lys Leu Lys Pro Ile Ile Phe Val Ile Cys
465                 470                 475                 480
Asn Asp Gly Phe Thr Ile Glu Arg Phe Ile His Gly Met Glu Ala Glu
                485                 490                 495
Tyr Asn Asp Ile Ala Asn Trp Asp Phe Lys Ala Leu Val Asp Val Phe
            500                 505                 510
Gly Gly Ser Lys Thr Ala Lys Lys Phe Ala Val Lys Thr Lys Asp Glu
        515                 520                 525
Leu Asp Ser Leu Leu Thr Asp Pro Thr Phe Asn Ala Ala Glu Cys Leu
    530                 535                 540
Gln Phe Val Glu Leu Tyr Met Pro Lys Glu Asp Ala Pro Arg Ala Leu
545                 550                 555                 560
Ile Met Thr Ala Glu Ala Ser Ala Arg Asn Asn Ala Lys Thr Glu
                565                 570                 575
```

<210> SEQ ID NO 20

<211> LENGTH: 1728
<212> TYPE: DNA
<213> ORGANISM: Unknown
<220> FEATURE:
<223> OTHER INFORMATION: Fungal isolate from soil sample
<220> FEATURE:
<221> NAME/KEY: CDS
<222> LOCATION: (1)...(1728)

<400> SEQUENCE: 20

```
atg gcc agc atc aac atc agg gtg cag aat ctc gag caa ccc atg gac    48
Met Ala Ser Ile Asn Ile Arg Val Gln Asn Leu Glu Gln Pro Met Asp
 1               5                  10                  15 gtt gcc gag tat ctt ttc cgg cgt ctc cac gaa atc ggc att cgc tcc    96
Val Ala Glu Tyr Leu Phe Arg Arg Leu His Glu Ile Gly Ile Arg Ser
             20                  25                  30 atc cac ggt ctt cca ggc gat tac aac ctt ctt gcc ctc gac tat ttg   144
Ile His Gly Leu Pro Gly Asp Tyr Asn Leu Leu Ala Leu Asp Tyr Leu
         35                  40                  45 cca tca tgt ggc ctg aga tgg gtt ggc agc gtc aac gaa ctc aat gct   192
Pro Ser Cys Gly Leu Arg Trp Val Gly Ser Val Asn Glu Leu Asn Ala
     50                  55                  60 gct tat gct gct gat ggc tat gcc cgc gtc aag cag atg gga gct ctc   240
Ala Tyr Ala Ala Asp Gly Tyr Ala Arg Val Lys Gln Met Gly Ala Leu
 65                  70                  75                  80 atc acc act ttt gga gtg gga gag ctc tca gcc atc aat ggc gtt gcc   288
Ile Thr Thr Phe Gly Val Gly Glu Leu Ser Ala Ile Asn Gly Val Ala
                 85                  90                  95 ggt gcc ttt tcg gaa cac gtc cca gtc gtt cac att gtt ggc tgc cct   336
Gly Ala Phe Ser Glu His Val Pro Val Val His Ile Val Gly Cys Pro
            100                 105                 110 tcc act gcc tcg cag cga aac ggc atg ctc ctc cac cac acg ctt gga   384
Ser Thr Ala Ser Gln Arg Asn Gly Met Leu Leu His His Thr Leu Gly
        115                 120                 125 aac ggc gac ttc aac atc ttt gcc aac atg agc gct caa atc tct tgc   432
Asn Gly Asp Phe Asn Ile Phe Ala Asn Met Ser Ala Gln Ile Ser Cys
    130                 135                 140 gaa gtg gcc aag ctc acc aac cct gcc gaa att gcg acc cag atc gac   480
Glu Val Ala Lys Leu Thr Asn Pro Ala Glu Ile Ala Thr Gln Ile Asp
145                 150                 155                 160 cat gcc ctc cgc gtt tgc ttc att cgt tct cgg ccc gtc tac atc atg   528
His Ala Leu Arg Val Cys Phe Ile Arg Ser Arg Pro Val Tyr Ile Met
                165                 170                 175 ctt ccc acc gat atg gtc cag gcc aaa gta gaa ggt gcc aga ctc aag   576
Leu Pro Thr Asp Met Val Gln Ala Lys Val Glu Gly Ala Arg Leu Lys
            180                 185                 190 gaa cca att gac ttg tcg gag cct cca aat gat ccc gag aaa gaa gca   624
Glu Pro Ile Asp Leu Ser Glu Pro Pro Asn Asp Pro Glu Lys Glu Ala
        195                 200                 205 tac gtc gtt gac gtt gtc ctc aag tac ctc cgt gct gca aag aac ccc   672
Tyr Val Val Asp Val Val Leu Lys Tyr Leu Arg Ala Ala Lys Asn Pro
    210                 215                 220 gtc atc ctt gtc gat gct tgt gct atc cgt cat cgt gtt ctt gat gag   720
Val Ile Leu Val Asp Ala Cys Ala Ile Arg His Arg Val Leu Asp Glu
225                 230                 235                 240 gtt cat gat ctc atc gaa aag aca aac ctc ccc gtc ttt gtc act cct   768
Val His Asp Leu Ile Glu Lys Thr Asn Leu Pro Val Phe Val Thr Pro
                245                 250                 255 atg ggc aaa ggt gct gtt aac gaa gaa cac ccg aca tat ggt ggt gtc   816
Met Gly Lys Gly Ala Val Asn Glu Glu His Pro Thr Tyr Gly Gly Val
            260                 265                 270
```

```
tat gcc ggt gac ggc tca cat ccg cct caa gtt aag gac atg gtt gag      864
Tyr Ala Gly Asp Gly Ser His Pro Pro Gln Val Lys Asp Met Val Glu
            275                 280                 285 tct tct gat ttg ata ttg aca atc ggt gct ctc aag agc gac ttc aac      912
Ser Ser Asp Leu Ile Leu Thr Ile Gly Ala Leu Lys Ser Asp Phe Asn
        290                 295                 300 act gct ggc ttc tct tac cgt acc tca cag ctg aac acg att gat cta      960
Thr Ala Gly Phe Ser Tyr Arg Thr Ser Gln Leu Asn Thr Ile Asp Leu
305                 310                 315                 320 cac agc gac cac tgc att gtc aaa tac tcg aca tat cca ggt gtc cag     1008
His Ser Asp His Cys Ile Val Lys Tyr Ser Thr Tyr Pro Gly Val Gln
                325                 330                 335 atg agg ggt gtg ctg cga caa gtg att aag cag ctc gat gca tct gag     1056
Met Arg Gly Val Leu Arg Gln Val Ile Lys Gln Leu Asp Ala Ser Glu
            340                 345                 350 atc aac gct cag cca gcg cca gtc gtc gag aat gaa gtt gcc aaa aac     1104
Ile Asn Ala Gln Pro Ala Pro Val Val Glu Asn Glu Val Ala Lys Asn
        355                 360                 365 cga gat aac tca ccc gtc att aca caa gct ttc ttc tgg ccg cgc gtg     1152
Arg Asp Asn Ser Pro Val Ile Thr Gln Ala Phe Phe Trp Pro Arg Val
370                 375                 380 gga gag ttc ctg aag aag aac gac atc gtc att acc gag act gga aca     1200
Gly Glu Phe Leu Lys Lys Asn Asp Ile Val Ile Thr Glu Thr Gly Thr
385                 390                 395                 400 gcc aac ttt ggc atc tgg gat act aag ttt ccc tct ggc gtt act gcg     1248
Ala Asn Phe Gly Ile Trp Asp Thr Lys Phe Pro Ser Gly Val Thr Ala
                405                 410                 415 ctt tct cag gtc ctt tgg gga agc att ggt tgg tcc gtt ggt gcc tgc     1296
Leu Ser Gln Val Leu Trp Gly Ser Ile Gly Trp Ser Val Gly Ala Cys
            420                 425                 430 caa gga gcc gtt ctt gca gcc gcc gat gac aac agc gat cgc aga act     1344
Gln Gly Ala Val Leu Ala Ala Ala Asp Asp Asn Ser Asp Arg Arg Thr
        435                 440                 445 atc ctc ttt gtt ggt gat ggc tca ttc cag ctc act gct caa gaa ttg     1392
Ile Leu Phe Val Gly Asp Gly Ser Phe Gln Leu Thr Ala Gln Glu Leu
450                 455                 460 agc aca atg att cgt ctc aag ctg aag ccc atc atc ttt gtc atc tgc     1440
Ser Thr Met Ile Arg Leu Lys Leu Lys Pro Ile Ile Phe Val Ile Cys
465                 470                 475                 480 aac gat ggc ttt acc att gaa cga ttc att cac ggc atg gaa gcc gag     1488
Asn Asp Gly Phe Thr Ile Glu Arg Phe Ile His Gly Met Glu Ala Glu
                485                 490                 495 tac aac gac atc gca aat tgg gac ttc aag gct ctg gtt gac gtc ttt     1536
Tyr Asn Asp Ile Ala Asn Trp Asp Phe Lys Ala Leu Val Asp Val Phe
            500                 505                 510 ggc ggc tct aag acg gcc aag aag ttc gcc gtc aag acc aag gac gag     1584
Gly Gly Ser Lys Thr Ala Lys Lys Phe Ala Val Lys Thr Lys Asp Glu
        515                 520                 525 ctg gac agc ctt ctc aca gac cct acc ttt aac gcc gca gaa tgc ctc     1632
Leu Asp Ser Leu Leu Thr Asp Pro Thr Phe Asn Ala Ala Glu Cys Leu
530                 535                 540 cag ttt gtc gag cta tat atg ccc aaa gaa gat gct cct cga gca ttg     1680
Gln Phe Val Glu Leu Tyr Met Pro Lys Glu Asp Ala Pro Arg Ala Leu
545                 550                 555                 560 atc atg acg gca gaa gct agc gcg agg aac aat gcc aag aca gag taa     1728
Ile Met Thr Ala Glu Ala Ser Ala Arg Asn Asn Ala Lys Thr Glu  *
                565                 570                 575

<210> SEQ ID NO 21
<211> LENGTH: 575
```

```
<212> TYPE: PRT
<213> ORGANISM: Unknown
<220> FEATURE:
<223> OTHER INFORMATION: Fungal isolate from soil sample

<400> SEQUENCE: 21
```

Met Ala Ser Ile Asn Ile Arg Val Gln Asn Leu Glu Gln Pro Met Asp
 1               5                  10                  15

Val Ala Glu Tyr Leu Phe Arg Arg Leu His Glu Ile Gly Ile Arg Ser
            20                  25                  30

Ile His Gly Leu Pro Gly Asp Tyr Asn Leu Leu Ala Leu Asp Tyr Leu
        35                  40                  45

Pro Ser Cys Gly Leu Arg Trp Val Gly Ser Val Asn Glu Leu Asn Ala
    50                  55                  60

Ala Tyr Ala Ala Asp Gly Tyr Ala Arg Val Lys Gln Met Gly Ala Leu
65                  70                  75                  80

Ile Thr Thr Phe Gly Val Gly Glu Leu Ser Ala Ile Asn Gly Val Ala
                85                  90                  95

Gly Ala Phe Ser Glu His Val Pro Val Val His Ile Val Gly Cys Pro
            100                 105                 110

Ser Thr Ala Ser Gln Arg Asn Gly Met Leu Leu His Thr Leu Gly
        115                 120                 125

Asn Gly Asp Phe Asn Ile Phe Ala Asn Met Ser Ala Gln Ile Ser Cys
    130                 135                 140

Glu Val Ala Lys Leu Thr Asn Pro Ala Glu Ile Ala Thr Gln Ile Asp
145                 150                 155                 160

His Ala Leu Arg Val Cys Phe Ile Arg Ser Arg Pro Val Tyr Ile Met
                165                 170                 175

Leu Pro Thr Asp Met Val Gln Ala Lys Val Glu Gly Ala Arg Leu Lys
            180                 185                 190

Glu Pro Ile Asp Leu Ser Glu Pro Asn Asp Pro Glu Lys Glu Ala
        195                 200                 205

Tyr Val Val Asp Val Val Leu Lys Tyr Leu Arg Ala Ala Lys Asn Pro
    210                 215                 220

Val Ile Leu Val Asp Ala Cys Ala Ile Arg His Arg Val Leu Asp Glu
225                 230                 235                 240

Val His Asp Leu Ile Glu Lys Thr Asn Leu Pro Val Phe Val Thr Pro
                245                 250                 255

Met Gly Lys Gly Ala Val Asn Glu Glu His Pro Thr Tyr Gly Gly Val
            260                 265                 270

Tyr Ala Gly Asp Gly Ser His Pro Pro Gln Val Lys Asp Met Val Glu
        275                 280                 285

Ser Ser Asp Leu Ile Leu Thr Ile Gly Ala Leu Lys Ser Asp Phe Asn
    290                 295                 300

Thr Ala Gly Phe Ser Tyr Arg Thr Ser Gln Leu Asn Thr Ile Asp Leu
305                 310                 315                 320

His Ser Asp His Cys Ile Val Lys Tyr Ser Thr Tyr Pro Gly Val Gln
                325                 330                 335

Met Arg Gly Val Leu Arg Gln Val Ile Lys Gln Leu Asp Ala Ser Glu
            340                 345                 350

Ile Asn Ala Gln Pro Ala Pro Val Val Glu Asn Glu Val Ala Lys Asn
        355                 360                 365

Arg Asp Asn Ser Pro Val Ile Thr Gln Ala Phe Phe Trp Pro Arg Val
    370                 375                 380

-continued

```
Gly Glu Phe Leu Lys Lys Asn Asp Ile Val Ile Thr Glu Thr Gly Thr
385                 390                 395                 400

Ala Asn Phe Gly Ile Trp Asp Thr Lys Phe Pro Ser Gly Val Thr Ala
                405                 410                 415

Leu Ser Gln Val Leu Trp Gly Ser Ile Gly Trp Ser Val Gly Ala Cys
            420                 425                 430

Gln Gly Ala Val Leu Ala Ala Ala Asp Asp Asn Ser Asp Arg Arg Thr
        435                 440                 445

Ile Leu Phe Val Gly Asp Gly Ser Phe Gln Leu Thr Ala Gln Glu Leu
        450                 455                 460

Ser Thr Met Ile Arg Leu Lys Leu Lys Pro Ile Ile Phe Val Ile Cys
465                 470                 475                 480

Asn Asp Gly Phe Thr Ile Glu Arg Phe Ile His Gly Met Glu Ala Glu
                485                 490                 495

Tyr Asn Asp Ile Ala Asn Trp Asp Phe Lys Ala Leu Val Asp Val Phe
            500                 505                 510

Gly Gly Ser Lys Thr Ala Lys Lys Phe Ala Val Lys Thr Lys Asp Glu
        515                 520                 525

Leu Asp Ser Leu Leu Thr Asp Pro Thr Phe Asn Ala Ala Glu Cys Leu
        530                 535                 540

Gln Phe Val Glu Leu Tyr Met Pro Lys Glu Asp Ala Pro Arg Ala Leu
545                 550                 555                 560

Ile Met Thr Ala Glu Ala Ser Ala Arg Asn Asn Ala Lys Thr Glu
                565                 570                 575
```